United States Patent
Stevens et al.

(10) Patent No.: US 7,811,312 B2
(45) Date of Patent: Oct. 12, 2010

(54) BONE ALIGNMENT IMPLANT AND METHOD OF USE

(75) Inventors: Peter M. Stevens, Salt Lake City, UT (US); Daniel F. Justin, Logan, UT (US)

(73) Assignee: Morphographics, LC, Salt Lake City, UT (US)

( * ) Notice: Subject to any disclaimer, the term of this patent is extended or adjusted under 35 U.S.C. 154(b) by 1594 days.

(21) Appl. No.: 10/310,720

(22) Filed: Dec. 4, 2002

(65) Prior Publication Data

US 2004/0111089 A1 Jun. 10, 2004

(51) Int. Cl.
*A61B 17/80* (2006.01)
(52) U.S. Cl. .................. 606/280; 623/13.12; 623/13.14
(58) Field of Classification Search ............. 606/69–71, 606/280–299; 623/13.11, 13.12, 13.14
See application file for complete search history.

(56) References Cited

U.S. PATENT DOCUMENTS

| | | | |
|---|---|---|---|
| 3,741,205 | A | 6/1973 | Markolf et al. |
| 3,939,828 | A | 2/1976 | Mohr |
| 3,988,783 | A | 11/1976 | Treace |
| 4,219,015 | A | 8/1980 | Steinemann |
| 4,434,796 | A | 3/1984 | Karapetian |
| 4,454,875 | A | 6/1984 | Pratt |
| 4,502,475 | A | 3/1985 | Weigle |
| 4,503,848 | A | 3/1985 | Caspar et al. |
| 4,570,623 | A | 2/1986 | Ellison |
| 4,790,297 | A | 12/1988 | Lugue |
| 4,841,960 | A | 6/1989 | Garner |
| 4,848,328 | A | 7/1989 | Laboureau |
| 4,852,558 | A | 8/1989 | Outerbridge |
| 4,905,679 | A | 3/1990 | Morgan |
| 4,966,599 | A | 10/1990 | Pollock |

(Continued)

FOREIGN PATENT DOCUMENTS

EP 0598573 A2 5/1994

(Continued)

OTHER PUBLICATIONS

Cary H. Mielke, M.D., et al., *Hemiepiphyseal Stapling for Knee Deformities in Children Younger than 10 Years: A Preliminary Report*, Journal of Pediatric Orthopaedics, vol. 16, No. 4, 1996, pp. 423-429.

(Continued)

*Primary Examiner*—Eduardo C Robert
*Assistant Examiner*—Mary Hoffman
(74) *Attorney, Agent, or Firm*—Workman Nydegger

(57) ABSTRACT

A bone alignment implant includes a first bone fastener with a first bone engager that is adapted for fixation into the metaphyseal bone and a second bone fastener with a second bone engager that is adapted for fixation into the metaphyseal bone. A link connecting the two fasteners spans across the physis. These implants act as a flexible tethers between the epiphyseal and the metaphyseal sections of bone during bone growth. These implants are designed to adjust and deform during the bone realignment process. When placed on the convex side of the deformity, the implant allows the bone on the concave side of the deformity to grow. During the growth process the bone is then realigned. A similar procedure is used to correct torsional deformities.

24 Claims, 22 Drawing Sheets

U.S. PATENT DOCUMENTS

| | | |
|---|---|---|
| 5,041,113 A | 8/1991 | Biedermann et al. |
| 5,053,038 A | 10/1991 | Sheenan |
| 5,180,393 A | 1/1993 | Commarmond |
| 5,190,545 A | 3/1993 | Corsi |
| 5,304,210 A | 4/1994 | Crook |
| 5,360,450 A | 11/1994 | Giannini |
| 5,366,479 A | 11/1994 | McGarry |
| 5,372,598 A | 12/1994 | Luhr et al. |
| 5,380,324 A | 1/1995 | Miller |
| 5,423,826 A | 6/1995 | Coates et al. |
| 5,449,359 A | 9/1995 | Groiso |
| 5,470,333 A | 11/1995 | Ray |
| 5,474,553 A | 12/1995 | Baumgart |
| 5,569,250 A | 10/1996 | Sarver |
| 5,586,985 A * | 12/1996 | Putnam et al. ............... 606/69 |
| 5,603,713 A | 2/1997 | Aust et al. |
| 5,607,430 A | 3/1997 | Bailey |
| 5,616,144 A * | 4/1997 | Yapp et al. ................... 606/61 |
| 5,662,655 A | 9/1997 | Laboureau |
| 5,676,667 A * | 10/1997 | Hausman .................... 606/69 |
| 5,688,283 A | 11/1997 | Knapp |
| 5,709,686 A | 1/1998 | Talos |
| 5,733,287 A | 3/1998 | Tepic |
| 5,735,875 A | 4/1998 | Bonutti |
| 5,746,742 A | 5/1998 | Runciman |
| 5,785,712 A | 7/1998 | Runciman et al. |
| 5,785,713 A | 7/1998 | Jobe |
| 5,788,698 A | 8/1998 | Savornin |
| 5,868,746 A | 2/1999 | Sarver |
| 5,904,683 A | 5/1999 | Pohndorf et al. |
| 5,947,999 A | 9/1999 | Groiso |
| 5,951,557 A | 9/1999 | Luter |
| 5,968,046 A | 10/1999 | Castleman |
| 6,001,099 A | 12/1999 | Huebner |
| 6,004,323 A | 12/1999 | Park |
| 6,017,345 A | 1/2000 | Richelsoph |
| 6,045,552 A | 4/2000 | Zucherman et al. |
| 6,053,919 A | 4/2000 | Talos |
| 6,139,550 A | 10/2000 | Michaelson |
| 6,159,213 A | 12/2000 | Rogozinski |
| 6,187,009 B1 | 2/2001 | Herzog |
| 6,214,012 B1 * | 4/2001 | Karpman et al. ............. 606/93 |
| 6,235,034 B1 * | 5/2001 | Bray .......................... 606/71 |
| 6,379,364 B1 | 4/2002 | Brace |
| 6,440,131 B1 | 8/2002 | Haidukewych |
| 6,454,769 B2 | 9/2002 | Wagner |
| 6,458,133 B1 | 10/2002 | Lin |
| D469,532 S | 1/2003 | Bryant et al. |
| 6,565,570 B2 | 5/2003 | Sterett et al. |
| 6,565,571 B1 * | 5/2003 | Jackowski et al. ........... 606/69 |
| 6,585,769 B1 * | 7/2003 | Muhanna et al. ......... 623/13.14 |
| 6,669,700 B1 * | 12/2003 | Farris et al. .................. 606/69 |
| 6,695,846 B2 | 2/2004 | Richelsoph et al. |
| 6,730,091 B1 | 5/2004 | Pfefferle et al. |
| 6,740,088 B1 | 5/2004 | Kozak et al. |
| 6,746,450 B1 * | 6/2004 | Wall et al. .................... 606/61 |
| 6,755,832 B2 | 6/2004 | Happonen et al. |
| 6,764,489 B2 | 7/2004 | Ferree |
| 6,773,437 B2 | 8/2004 | Ogilvie et al. |
| 6,793,658 B2 * | 9/2004 | LeHuec et al. ............... 606/61 |
| 6,830,571 B2 | 12/2004 | Lenke et al. |
| 7,048,739 B2 | 5/2006 | Konieczynski et al. |
| 2001/0014807 A1 | 8/2001 | Wagner |
| 2001/0037112 A1 | 11/2001 | Brace |
| 2002/0058939 A1 | 5/2002 | Wagner |
| 2002/0077630 A1 | 6/2002 | Lin |
| 2003/0004515 A1 | 1/2003 | Curtis |
| 2004/0019353 A1 | 1/2004 | Fried et al. |
| 2004/0181226 A1 | 9/2004 | Michelson |
| 2004/0210218 A1 | 10/2004 | Dixon et al. |
| 2005/0149023 A1 | 7/2005 | Ritland |
| 2005/0192577 A1 | 9/2005 | Mosca et al. |
| 2007/0093838 A1 | 4/2007 | Khodadadyan-Klostermann et al. |
| 2008/0161816 A1 | 7/2008 | Stevens et al. |

FOREIGN PATENT DOCUMENTS

| | | | |
|---|---|---|---|
| EP | 0486762 B1 | 5/1995 | |
| EP | 0599640 B1 | 8/1998 | |
| EP | 0684017 B1 | 2/1999 | |
| FR | 2709410 A1 * | 3/1995 | ............... 606/75 |
| TW | 537025 | 6/2003 | |
| WO | WO9303681 A1 | 3/1993 | |
| WO | WO00/22999 * | 4/2000 | ............... 606/69 |
| WO | WO01/03570 * | 1/2001 | ............... 606/61 |
| WO | WO0119267 A1 | 3/2001 | |
| WO | WO0191660 A1 | 12/2001 | |

OTHER PUBLICATIONS

Peter M. Stevens, M.D., et al., *Physeal Stapling for Idiopathic Genu Valgum*, Journal of Pediatric Orthopaedics, vol. 19, No. 5, 1999, pp. 645-649.

Andrea Kramer, M.D., et al., *Anterior Femoral Stapling*, Journal of Pediatric Orthopaedics, vol. 21, No. 6, 2001, pp. 804-807.

J. Richard Bowen, M.D. et al., *Partial Epiphysiodesis at the Knee to Correct Angular Deformity*, Clinical Orthopaedics and Related Research, No. 198, Sep. 1985, pp. 184-190.

S.T. Canale, M.D., et al.; *Percutaneous Epiphysiodesis: Experimental Study and preliminary Clinical Results*, Journal of Pediatric Orthopedics, vol. 6, No. 2, 1986, pp. 150-156.

James W. Ogilvie, M.D., *Epiphysiodesis: Evaluation of a new Technique*, Journal of Pediatric Orthopedics, vol. 6, No. 2, 1986, pp. 147-149.

D. B. Phemister, *Operative Arrestment of Longitudinal Growth of Bones in the treatment of Deformities*, The Journal of Bone and Joint Surgery, vol. XV, No. 1, Jan. 1933, pp. 1-15.

Walter P. Blount, M.D., et al., *Control of Bone Growth by Epiphyseal Stapling: A Preliminary Report*, The Journal of Bone and Joint Surgery, vol. 31-A, No. 3, Jul. 1949, pp. 646-478, 953.

Walter P. Blount, M.D., *A Mature Look at Epiphyseal Stapling*, Clinical Orthopaedics and Related Research, Section II, No. 77, Jun. 1971, pp. 159-163.

Charles H. Frantz, M.D., *Epiphyseal Stapling: A Comprehensive Review*, Clinical Orthopaedics and Related Research, No. 77, Jun. 1971, pp. 149-157.

R.K. Fraser et al., *Medical Physeal Stapling for Primary and Secondary Genu Valgum in Late Childhood and Adolescence*, The Journal of Bone and Joint Surgery, vol. 77-B, No. 5, Sep. 1995, pp. 733-735.

Jean-Paul Metaizeau, M.D., et al., *Percutaneous Epiphysiodesis Using Transphyseal Screws (PETS) [Limb-Length Discrepancy]*, Journal of Pediatric Orthopaedics, vol. 18, No. 3, May/Jun. 1998.

ISA, PCT—Notification of transmittal of the International Search Report and the Written Opinion of the International Searching Authority, or the Declaration, Form PCT/ISA/220, International Application No. PCT/US2006/038773 dated Aug. 17, 2007.

Office Action dated Sep. 5, 2008 issued in U.S. Appl. No. 11/244,879.

Office Action dated Apr. 16, 2009 issued in U.S. Appl. No. 11/244,879.

* cited by examiner

BONE ALIGNMENT IMPLANT AND METHOD OF USE

CROSS-REFERENCE TO RELATED APPLICATIONS

Not applicable.

BACKGROUND OF THE INVENTION

1. The Field of the Invention

The present invention relates to the design and method of use for an implant to help realign angular and rotational deformities in long bones in patients with active growth plates.

2. Related Technology

As a result of congenital deformation, traumatic injury or other causes, long bones such as the femur, tibia and humerus may grow out of alignment, causing deformity of the limb and biomechanical abnormalities. While some deformities are asymptomatic or may resolve spontaneously, it is often necessary to intervene surgically to realign these limbs. For the patients requiring surgical intervention, both osteotomy with realignment of the bone and epiphyseal stapling are currently accepted methods of treatment.

One common method of surgical bone realignment is by means of an osteotomy, or cutting of the bone, followed by realignment of the bone. In some procedures the bone is cut laterally, transverse to the longitudinal axis of the bone. Then the bone is realigned. A bone graft is then placed in the resulting wedge space. The bone and the bone graft are stabilized by orthopedic fragment fixation implants such as screws and bone plates. In an alternative osteotomy procedure, a bone wedge is removed. The bone is realigned, and similar implants are used to secure the bone. A third method of deformity correction via osteotomy is to first cut the bore, then apply an external frame attached to pins drilled through the skin and into the bone. By adjusting the frame, either intraoperatively or postoperatively, the bone is straightened.

Because osteotomy methods require a relatively large incision to create bone cuts, they are relatively invasive; they disrupt the adjacent musculature and may pose a risk to the neurovascular structures. An additional disadvantage of these procedures is the potential risk of damage to the growth plate, resulting in the disruption of healthy limb growth. Consequently, this procedure may be reserved for bone alignment in skeletally mature patients in whom the growth plates are no longer active.

One less invasive method of bone alignment involves the placement of constraining implants such as staples around the growth plate of the bone to restrict bone growth at the implant site and allow the bone to grow on the opposite side. First conceived in 1945 by Dr. Walter Blount, this method is known as epiphyseal stapling. Typically epiphyseal stapling is more applicable in young pediatric patients and adolescents with active growth plates. A staple is placed on the convex side of an angular deformity. Since the bone is free to grow on the concave side of the deformity, the bone tends to grow on the unstapled side, causing the bone to realign over time. Once the bone is aligned, the constraining implants are typically removed.

As long as the growth plate is not disturbed, this type of intervention is generally successful. However, the procedure must be done during the time that the bone is still growing, and the physiodynamics of the physis (growth plate) must not be disturbed. With proper preoperative planning and placement of the implants, the surgeon can use the implants to slowly guide the bone back into alignment.

The implants currently used in epiphyseal stapling procedures are generally U-shaped, rigid staples. The general design has essentially remained the same as those devised by Blount in the 1940's. Since these implants are rigid, they act as three-dimensional constraints prohibiting expansion of the growth plate. They are not designed to allow flexibility or rotation of the staple legs with the bone sections as the bone is realigned. Due to the constraints of these staple implants, the planning associated with the placement of the implants is overly complicated. Consequently, the surgeon must not only determine where to position the implant across the physis, but also must account for the added variables of implant stiffness, implant strength and bone-implant interface rupture.

The force associated with bone growth causes bending of these implants proportionate to their stiffness. Depending on the strength of the implant, these loads could eventually cause the implants to fracture under the force of bone realignment. This can make them difficult or impossible to remove. These same forces can also cause the implants to deform, weakening the bone-to-implant interface. This weakening may result in migration of the implant out of the bone, risking damage to the adjacent soft tissues and failure of the procedure.

SUMMARY OF THE INVENTION

The invention relates to an orthopedic bone alignment implant system that includes a guide wire, a link and bone fasteners. The guide wire serves to locate the growth plate under fluoroscopic guidance. The bone fasteners and the link function together as a tether between bone segments on opposite sides of the physis. As the bone physis generates new physeal tissue, the bone alignment implant tethers between engagers on the bone segments. This tethering principle guides the alignment of the bone as it grows.

Although applicable in various orthopedic procedures involving fracture fixation, the bone alignment implant is also applicable to the correction of angular deformities in long bones in which the physis is still active.

The distal end of the guide wire is used to locate the physis. Once its tip is placed in the physis, it is driven partly into the physis to function as a temporary guide for the link. The delivery of the implant over the guide wire assures that the link is properly placed with the bone fasteners on opposite sides of the physis. This will minimize the chance of damaging the physis throughout bone realignment. The link is then placed over the guide wire and oriented such that openings through the link for the bone fasteners are on either side of the physis. For pure angular correction, these openings would be collinear with the long axis of the bone; for rotational correction, they would be oblique to its axis.

The bone fasteners are then placed through the openings in the link and into the bone, connecting the sections of bone on opposite sides of the physis with the implant. Alternatively, guide pins can be used to help align canullated fasteners.

The implant is designed such that it partially constrains the volume of the bone growth on the side of the physis that it is placed. The implant guides the growth of new bone at the physis such that the growth direction and resulting alignment is controlled. The implant limits the semi-longitudinal translation of the bone fasteners yet allows for the bone fasteners to freely rotate with the bone segments as the angular or torsional deformity is straightened.

In some embodiments of this invention, both the link and the fasteners are rigid, but the connection between them allows for relative movement of the fasteners. In other embodiments the link is flexible allowing the fasteners to move with the bone sections. In other embodiments, the fasteners have flexible shafts allowing only the bone engager of the fasteners to move with the bone sections. In still other embodiments, both the link and the shafts of the fasteners are flexible, allowing movement of the bone sections.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
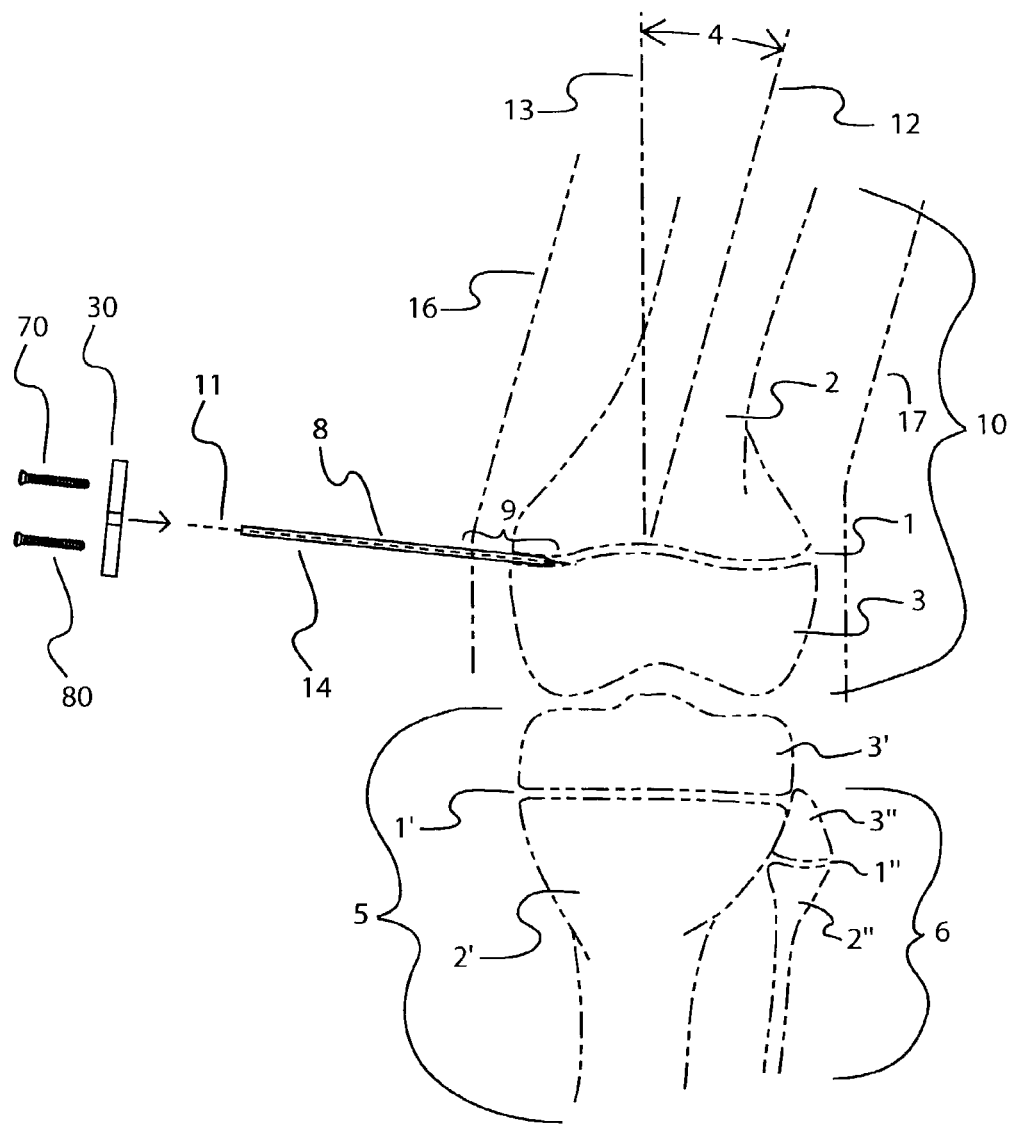
FIG. 1 is an anterior view of the knee showing a genu valgum deformity (knee knocking) in the femur and the insertion of a guide wire approximately parallel to the physis.

Referring to FIG. 1, a schematic anterior view of the human knee joint is depicted in which a distal femur 10 is proximal to a proximal tibia 5 and a proximal fibula 6. A distal femoral physis 1, or growth plate, separates a distal epiphyseal section 3 from a proximal metaphyseal section 2 of the distal femur 10. Likewise a proximal tibial physis 1' separates a proximal epiphyseal section 3' from a metaphyseal section 2' of the proximal tibia 5 and a proximal fibula physis 1" separates a proximal epiphyseal section 3" of a proximal fibula 6 from a metaphyseal section 2" of the proximal fibula 6. Although the invention described herein is adaptable to nearly all of the long bones in the body, only the example of correcting one type of an angular deformity in the distal femur will be described in detail. The principles described herein can be adapted to other deformities and other bones such as the tibia, fibula, humerus, radius and ulna.

By example, an angular deformity 4 in the femur 10 known as genu valgum or knock-knee is shown in FIG. 1. The angular deformity 4 is the angle between a pretreatment longitudinal axis 12 of the femur 10 and a post treatment projected longitudinal axis 13 of the femur 10. A bone alignment implant will be placed on the medial side of the femur 10. In this case, the medial side of the femur 10 is curved in a convex arc. Hence, this side of the deformity is called a convex side 16 because the angular deformity 4 bends the femur 10 in a curve that is angled away from or convex with respect to the medial side. A concave side 17 is on the opposite side of the femur 10. Likewise, the angular deformity 4 is angled towards the concave side 17.

A guide wire 8, as shown in FIG. 1, is used to locate the physis and guide the bone alignment implant to the surgical site. The guide wire 8 comprises a long axis 11, a distal section 9 that is shaped to fit into the physeal tissue, and a periphery 14 that is typically a constant size and shape. In this case, the shape of the guide wire 8 along the long axis 11 is essentially cylindrical so the shape of the periphery 14 is round and does not change except for in the distal section 9. However, the periphery 14 can be a variable cross-section that changes shape or size along the length of the long axis 11.

In this example, the long axis 11 of the guide wire 8 is placed into and approximately parallel with the physis 1 and is aligned approximately in the same plane as the angular deformity 4. As shown in FIG. 1, the distal section 9 of the guide wire 8 is partly inserted into the physis 1. Since the cartilaginous physis 1 is of less density than the surrounding bone, the surgeon can either poke the distal section of the guide wire 8 into the bone until the physis 1 is located, or the surgeon can use fluoroscopic x-ray (not shown) or other bone density detection means (not shown) to determine the location of the physis 1 relative to the distal section of the guide wire 8 to place the guide wire 8 in a direction that is approximately parallel with the physis 1.

Figure 2:
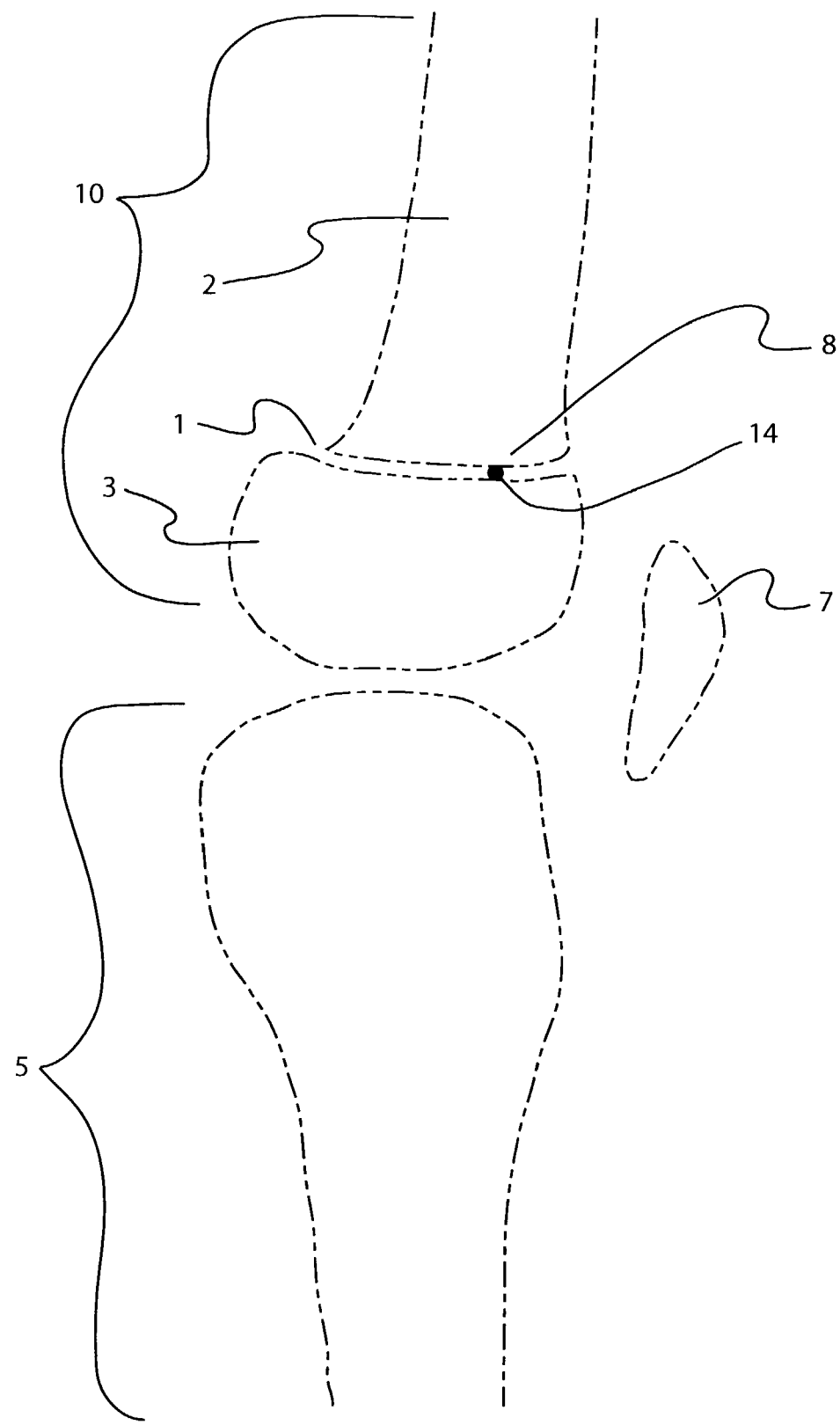
FIG. 2 is a sagittal view of that described in FIG. 1 showing the placement of the guide wire in the physis.

FIG. 2 is a sagittal view approximately perpendicular to the anterior view described in FIG. 1. For reference, a patella 7 is shown on the anterior side of the femur 10 and tibia 5. For clarity, in this example the guide wire 8 is straight and has a constant round outer periphery 14. Consequently, only the outer periphery 14 of the guide wire 8 is shown and appears as a circle in FIG. 2. FIG. 2 shows the placement of the guide wire 8 in the physis between the femoral metaphyseal section 2 and the distal femoral epiphyseal section 3. This is the preferred placement of the guide wire 8. The guidewire 8 is used to locate an area in the physis that will eventually be bridged by the bone alignment implant 9 that will tether between two sections of the bone. In FIG. 2, the two sections of bone that will be tethered by the bone alignment implant 9 are the distal femoral proximal epiphyseal section 3 and the femoral metaphyseal section 2.

Figure 3:
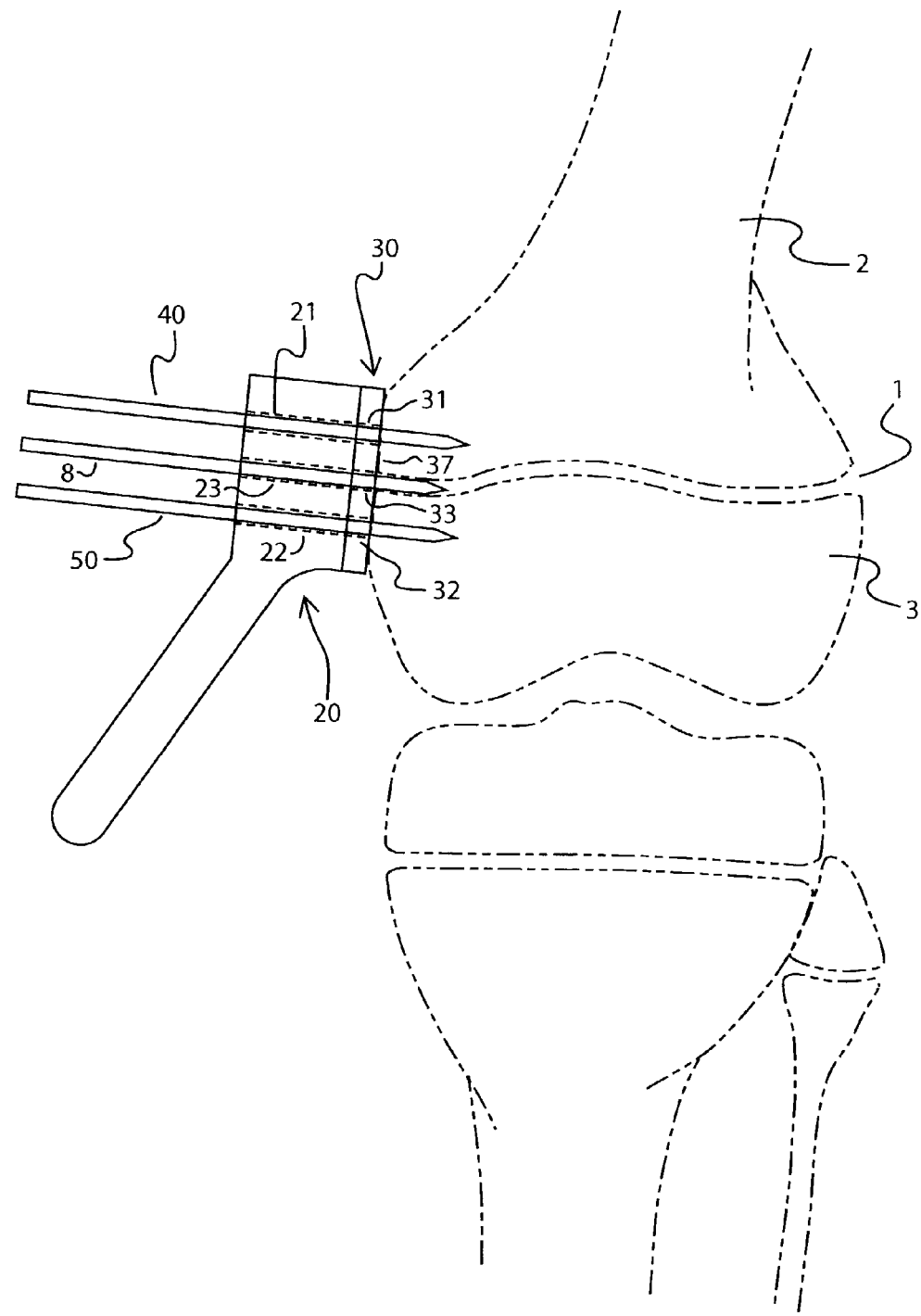
FIG. 3 is anterior view of the knee showing the placement of a link and drill guide over the guide wire and the use of the guide to place two guide pins for fasteners on opposite sides of the physis.

FIG. 3 is an anterior view of the knee showing the placement of a link 30 and a guide 20 over the guide wire 8. The guide 20 is used to place a first guide pin 40 and a second guide pin 50 on opposite sides of the physis 1. The link 30 has an outer periphery 34 that defines the outer material bounds of the link 30, a bone side 37 that is the side of the link that is placed against the bone, a first opening 31 and a second opening 32.

First, the guide 20 and link 30 are placed over the guide wire 8 by guiding the guide wire 8 over a guide opening 33 in the link 30 and the guide hole 23 in the guide 20. Then the first guide pin 40 is driven through a first hole 21 in the guide 20 and through the first opening 31 in the link 30 into the metaphyseal bone 2, and the second guide pin 50 is driven through a second hole 22 in the guide 20 and the second opening 32 in the link 30 into the distal epiphyseal section 3. Once the first guide pin 40 and the second guide pin 50 are placed, the guide 20 is removed.

Figure 4:
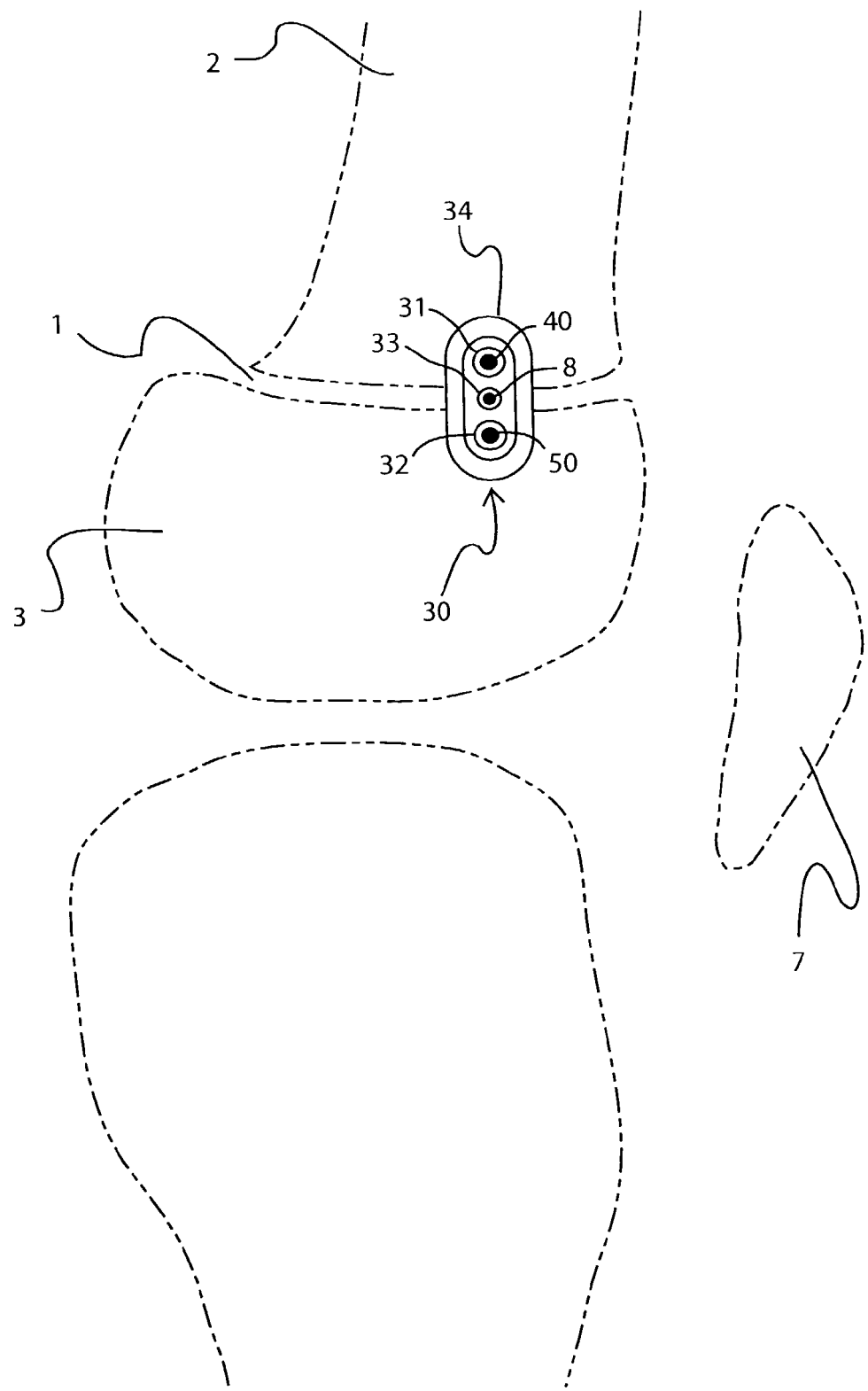
FIG. 4 is a sagittal view of the placement of the link described in FIG. 3 showing the position of the two guide pins on opposite sides of the physis.

FIG. 4 is a sagittal view of the placement of the link 30 described in FIG. 3. The position of the first guide pin 40 is through the first opening 31 in the link 30. The position of the second guide pin 50 is though the second opening 32 in the link 30. The guide pin 40 and guide pin 50 are on opposite sides of physis 1. Likewise, the first opening 31 and the second opening 32 are on opposite sides of the physis 1.

Figure 5:
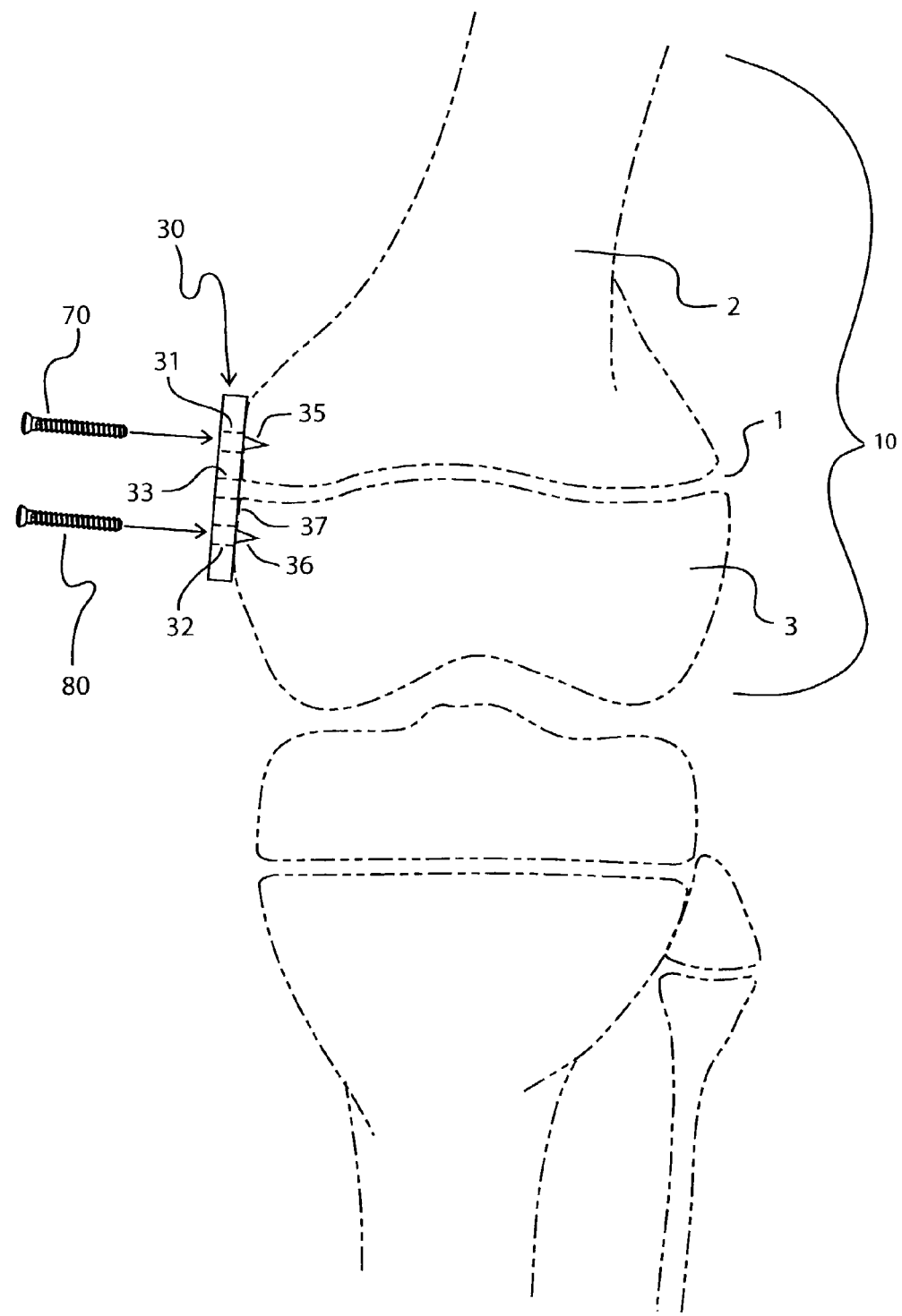
FIG. 5 is an alternative method of applying the link over the guide wire in which the link is placed first, then the fasteners are placed through the openings in the link.

FIG. 5 is an anterior view showing an alternative embodiment of the link 30 placed on the medial femur 10. In this embodiment, a first set of spikes 35 and a second set of spikes 36 on the bone side 37 of the link 30 help to keep the link 30 in place prior to the placement of a first bone fastener 70 and a second bone fastener 80. The first set of spikes 35 is positioned near the first opening 31 and the second set of spikes 36 is positioned near the second opening 32 in the link 30. Hence, as the link 30 is placed across the physis 1, the first set of spikes 35 contacts the metaphyseal section 2 and the second set of spikes 36 contacts the epiphyseal section 3. In this embodiment, the first bone fastener 70 is placed though the first opening 31 in the link 30 then into the metaphyseal section 2 and the second bone fastener 80 is placed through the second opening 32 in the link 30 then into the epiphyseal section 3.

Figures 6, 6A:
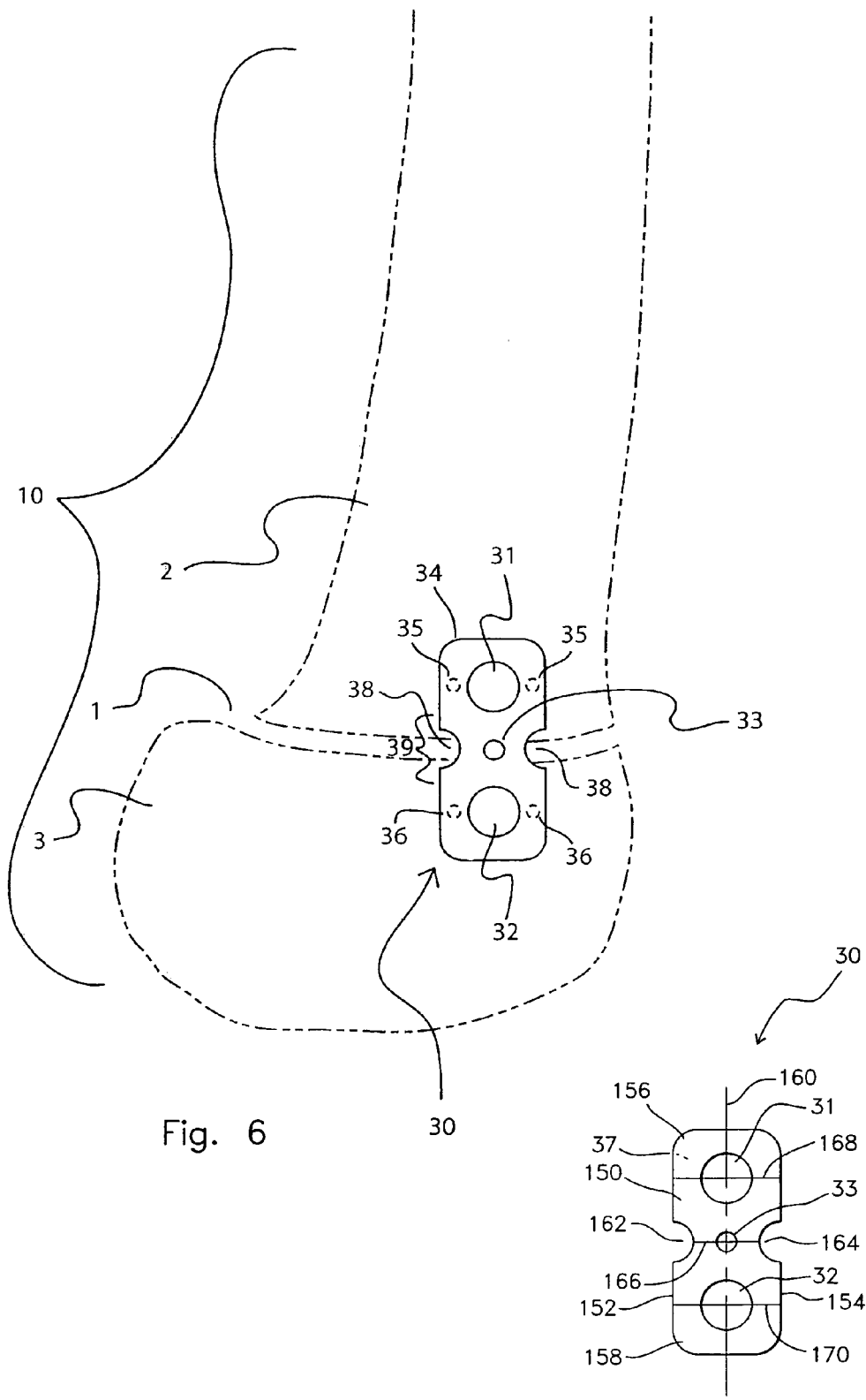
FIG. 6 is a sagittal view of the link placement also shown in FIG. 5.
FIG. 6A is a top plan view of the link shown in FIG. 6.

FIG. 6 is a sagittal view of the link 30 on the femur 10 showing the location of the first set of spikes 35 near the first opening 31 on the metaphyseal section 2 side of the physis 1 and the location of the second set of spikes near the second opening 32 on the epiphyseal section 3 side of the physis 1.

As shown in FIG. 6A, link 30 can further be defined as having a top surface 150 that is opposite the bottom surface 37. Bottom surface 37 was also previously referenced as bone side 37 in FIG. 3. Both bottom surface 37 and top surface 150 extend between a first side edge 152 and an opposing second side edge 154. Likewise, both bottom surface 37 and top surface 150 longitudinally extend between a first end 156 and an opposing second end 158. A first recess 162 is centrally formed on first side edge 152 while a second recess 164 is centrally formed on second side edge 154.

In the embodiment depicted, guide opening 33 is centrally disposed between first opening 31 and second opening 32 with guide opening 33 being smaller than openings 31 and 32. Each of openings 31, 32, and 33 are aligned along a central longitudinal axis 160 that extends between first end 156 and second end 158. Recesses 162 and 164 can be positioned on opposing sides of guide opening 33 such that a linear line 166 extending between recesses 162 and 164 intersect guide opening 33. The length of linear line 166 extending between recesses 162 and 164 is a first width of link 30. Linear line 166 is shown in the present embodiment as extending orthogonal to longitudinal axis 160.

Link 30 can also be formed so that a linear line 168 can extend between side edges 152 and 154 so as to intersect with first opening 31. Line 168 is shown extending orthogonal to longitudinal axis 160 and measures a second width of link 30. Because of recesses 162 and 164, the first width is smaller than the second width. A linear line 170 can similarly extend between side edges 152 and 154 so as to intersect with second opening 32. Line 170 is shown extending orthogonal to longitudinal axis 160 and measures a third width of link 30. The first width of link 30 is smaller than the than the third width.

Figure 7:
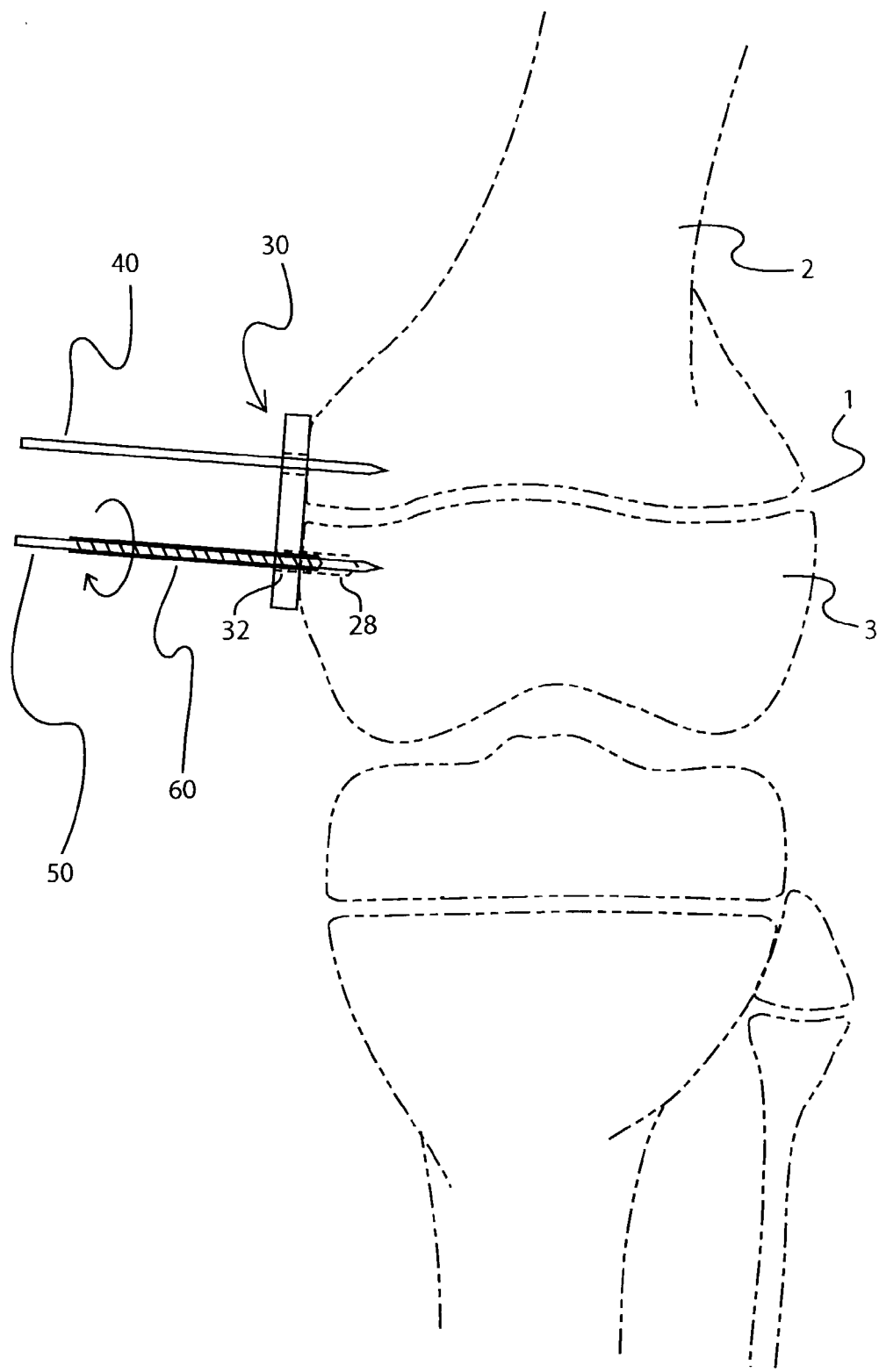
FIG. 7 is an anterior view showing an alternative method of drilling of holes in the bone over the guide pins to prepare the bone for the fasteners.

FIG. 7 is an anterior view of the placement of the link 30, first guide pin 40, and second guide pin 50 as previously described in the sagittal view shown in FIG. 4. FIG. 7 also shows a bone preparation tool 60 that can be used to prepare a bore 28 in the bone prior to the first fastener 70 or second fastener 80 placements. The bone preparation tool 60 can be a drill, tap, rasp, reamer, awl or any tool used to prepare a bore in bone tissue for a fastener. The bone preparation tool 60 is used to prepare a bore 28 on the bone near the second opening in the epiphyseal section 3 for the second fastener 80. A bone preparation tool 60 can also be used to prepare the bone in the metaphyseal section 2 for the first fastener 70. In the case of the example shown in FIG. 7, the bone preparation tool 60 is placed over the second guide pin 50, through the second opening 32, and into the epiphyseal section 3. However, the bone preparation tool 60 can also be placed directly through the second opening 32 without the guidance of the second guide pin 50. The bone preparation tool 60 is used if needed to prepare the bone to receive the first fastener 70 and second fastener 80. Once the bone is prepared, the bone preparation tool 60 is removed from the surgical site.

The first fastener 70 is then placed over the first guide pin 40, through the first opening 31, and into the metaphyseal section 2. The second fastener 80 is placed over the second guide pin 50, through the second opening 32 and into the epiphyseal section 3. If the first guide pin 40 and second guide pin 50 are not used, the first fastener 70 is simply driven through the first opening 31 and the second fastener 80 is simply driven though the second opening 32 without the aid of the guide pins 40 and 50.

Figure 8:
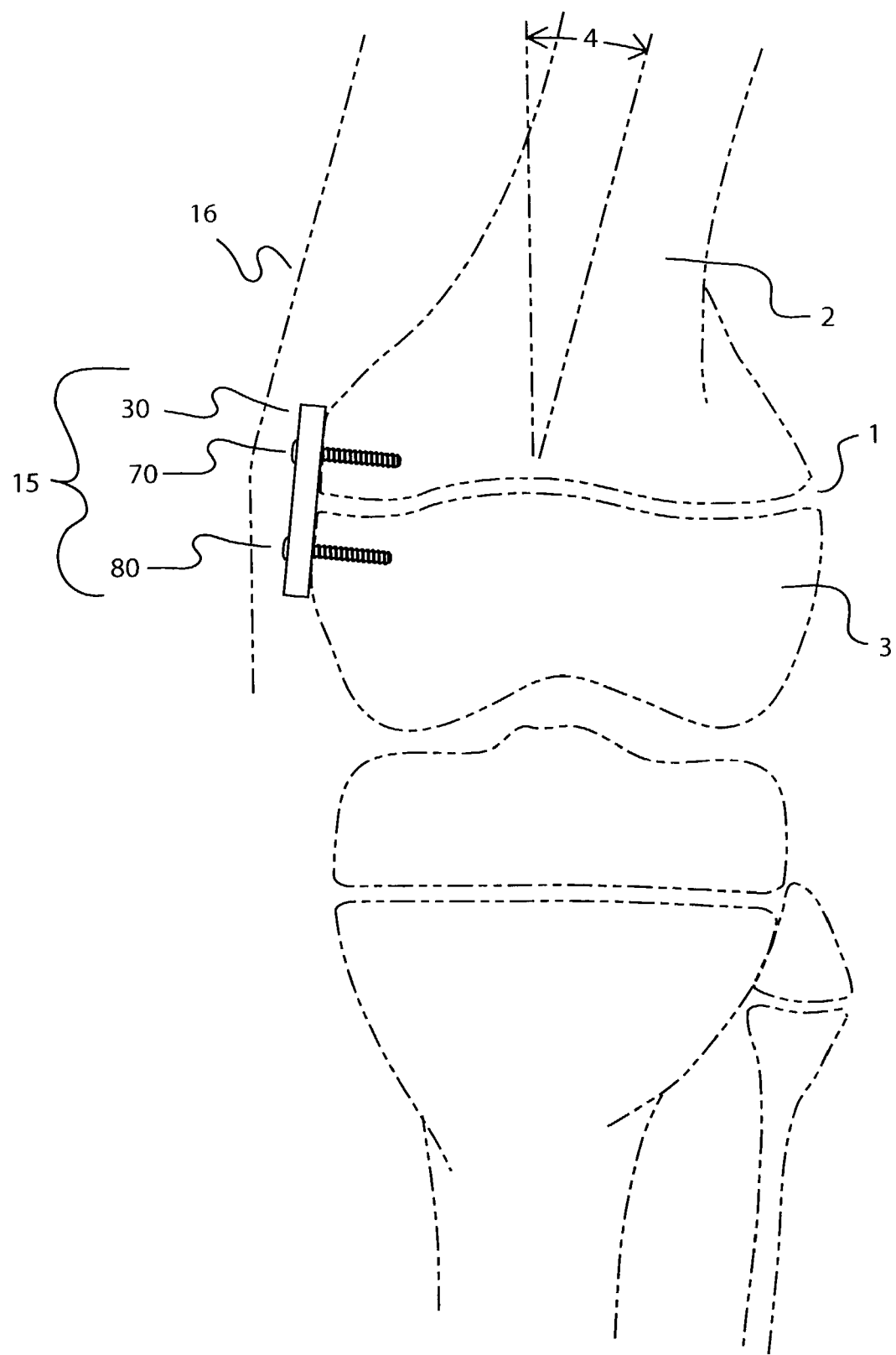
FIG. 8 is a anterior view of the link showing the placement of the fasteners through the link and into the bone segments.

FIG. 8 is an anterior view showing the position of a bone alignment implant 15 on the convex side 16 of the angular deformity 4. The bone alignment implant 15 comprises the link 30, the first fastener 70, and the second fastener 80. The bone alignment implant 15 functions as a tether connecting the metaphyseal section 2 and the epiphyseal section 3. The first fastener 70 and the second fastener 80 are placed on opposite sides of the physis 1. As the physis 1 generates new physeal tissue 90, the physeal tissue 90 will fill in between the metaphyseal section 2 and the epiphyseal section 3 in the space subjected to the least resistance. The bone alignment implant 15 restricts the longitudinal movement between the epiphyseal section 3 and the metaphyseal section 3 on the convex side 16 of the angular deformity 4.

Figure 9:
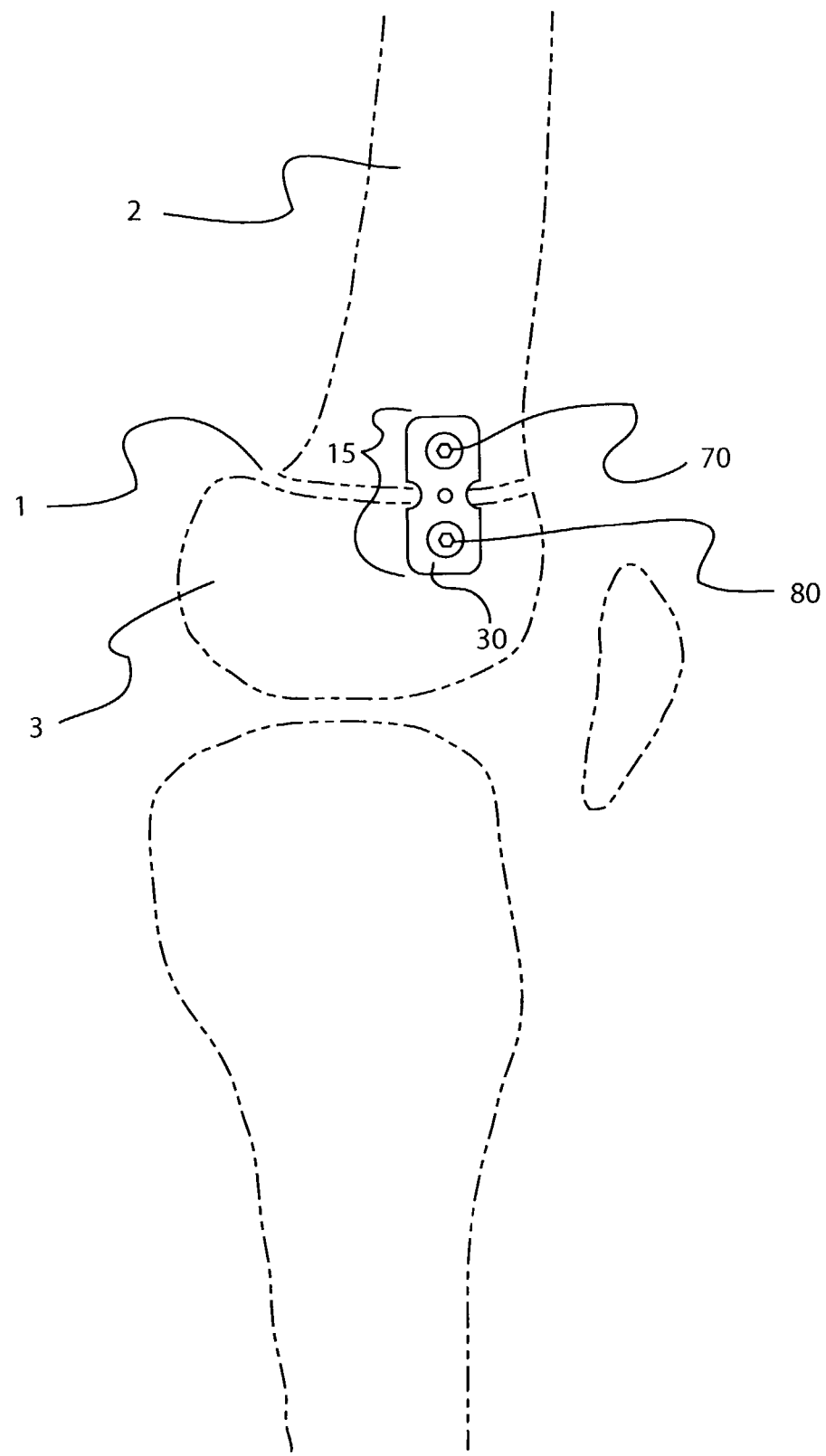
FIG. 9 is a sagittal view of the fasteners and link described in FIG. 8.

FIG. 9 shows the sagittal view of that described for FIG. 8. The bone alignment implant 15 functioning as a tether restricting the longitudinal movement between the epiphyseal section 3 and the metaphyseal section 2.

Figure 10:
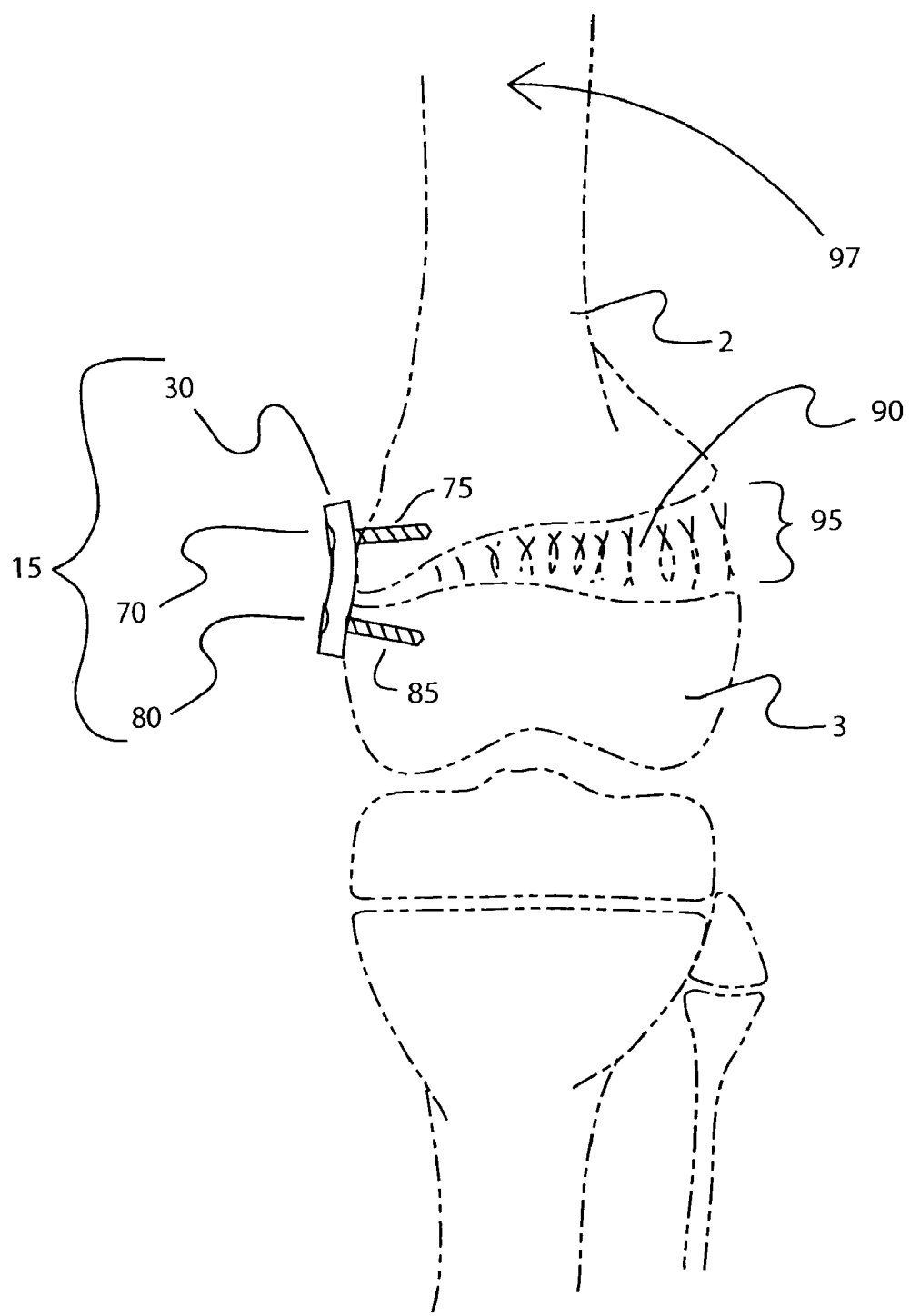
FIG. 10 is an anterior view as seen after the physeal tissue has grown and the bone alignment implant assembly has been reoriented as the bone is realigned.

As shown in FIG. 10, in a patient with an active physis, the newly generated physeal tissue 90 fills in more on the side of the bone that is not tethered by the bone alignment implant 15. Hence, a net gain 95 of physeal tissue 90 forces the bone to align in the direction of an angular correction 97.

Select embodiments of the bone alignment implant 15 comprise the first fastener 70 having a first engager 75, the second fastener 80 having a second engager 85 and the link 30. The link 30, the first fastener 70 and the second fastener 80 function together as tethers between a first engager 75 on the first fastener 70 and a second engager 85 on the second fastener 80, guiding movement between the epiphyseal section 3 and metaphyseal section 2 of bone.

Figure 11:
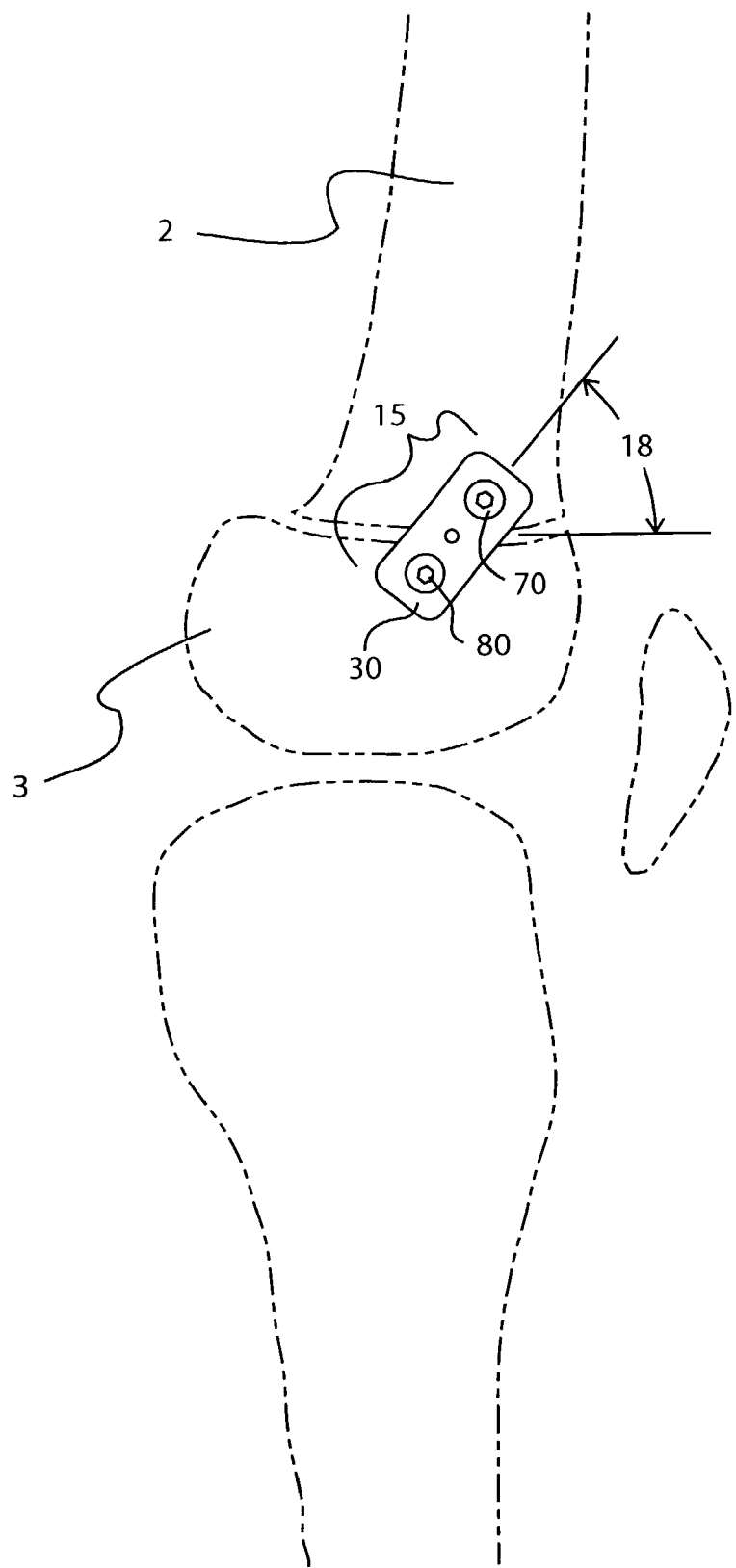
FIG. 11 is sagittal view of the bone alignment implant placed on a rotational deformity.
Figure 12:
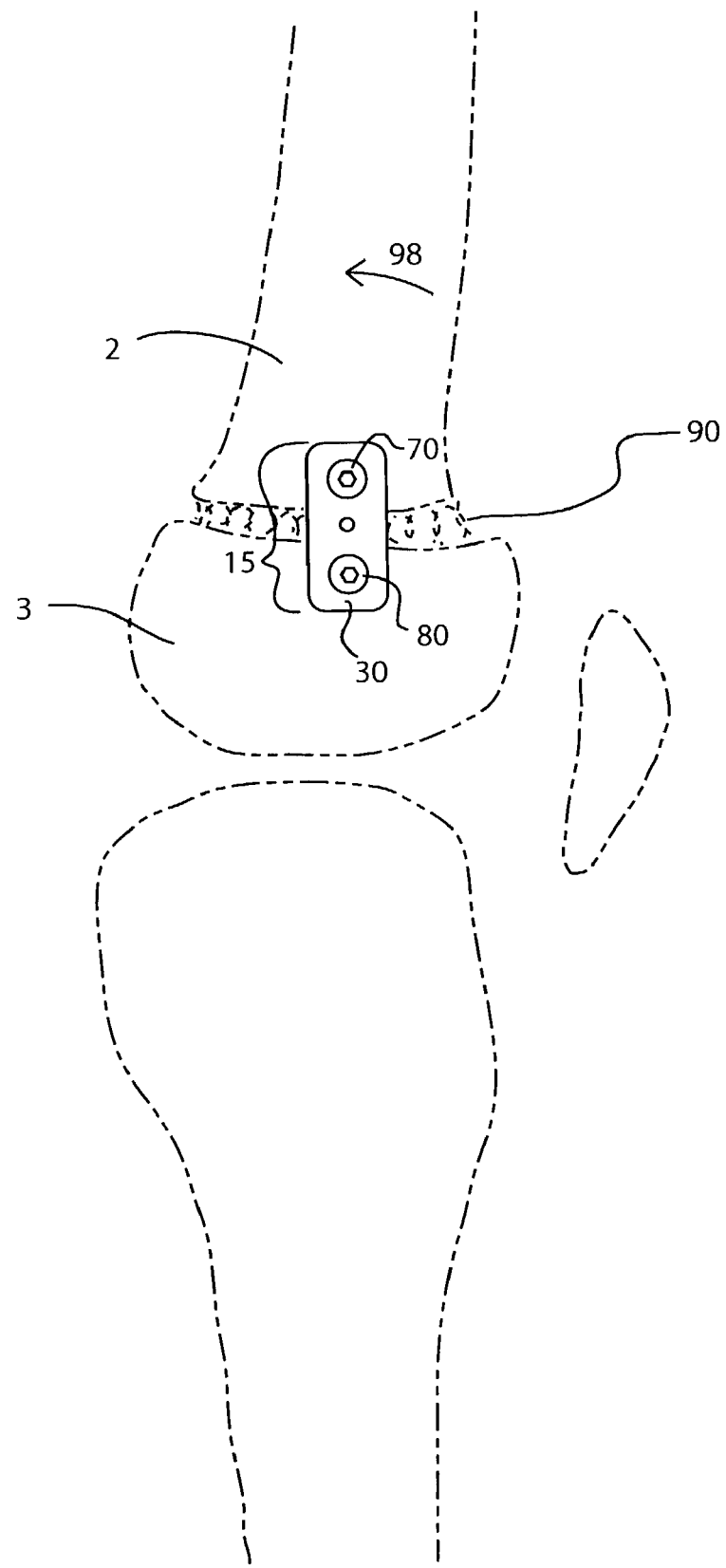
FIG. 12 is the same sagittal view described in FIG. 12 after the rotational deformity has been corrected.

FIG. 11 and FIG. 12 show an example of using the bone alignment implant to correct a torsional abnormality between the metaphyseal section 2 and the epiphyseal section 3. The link 30 is placed across the physis 1 at an angle 18 that is related to the amount of torsional deformity between the bone sections 2 and 3. As the physis 1 generates new physeal tissue 90, the bone alignment implant 15 guides the direction of growth of the bone to allow a torsional correction 98 of the bone alignment.

Figure 13:
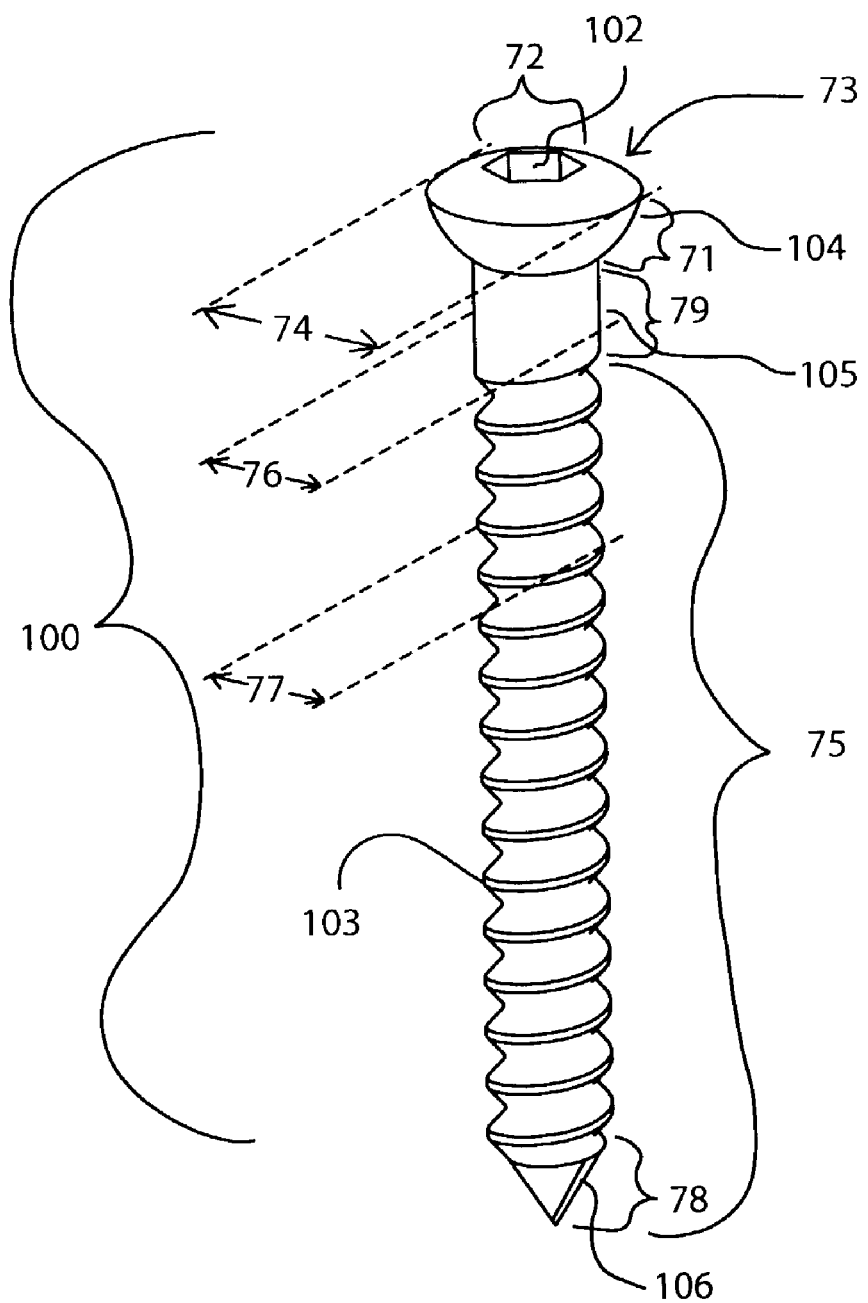
FIG. 13 is a perspective view of a threaded fastener.
Figure 14:
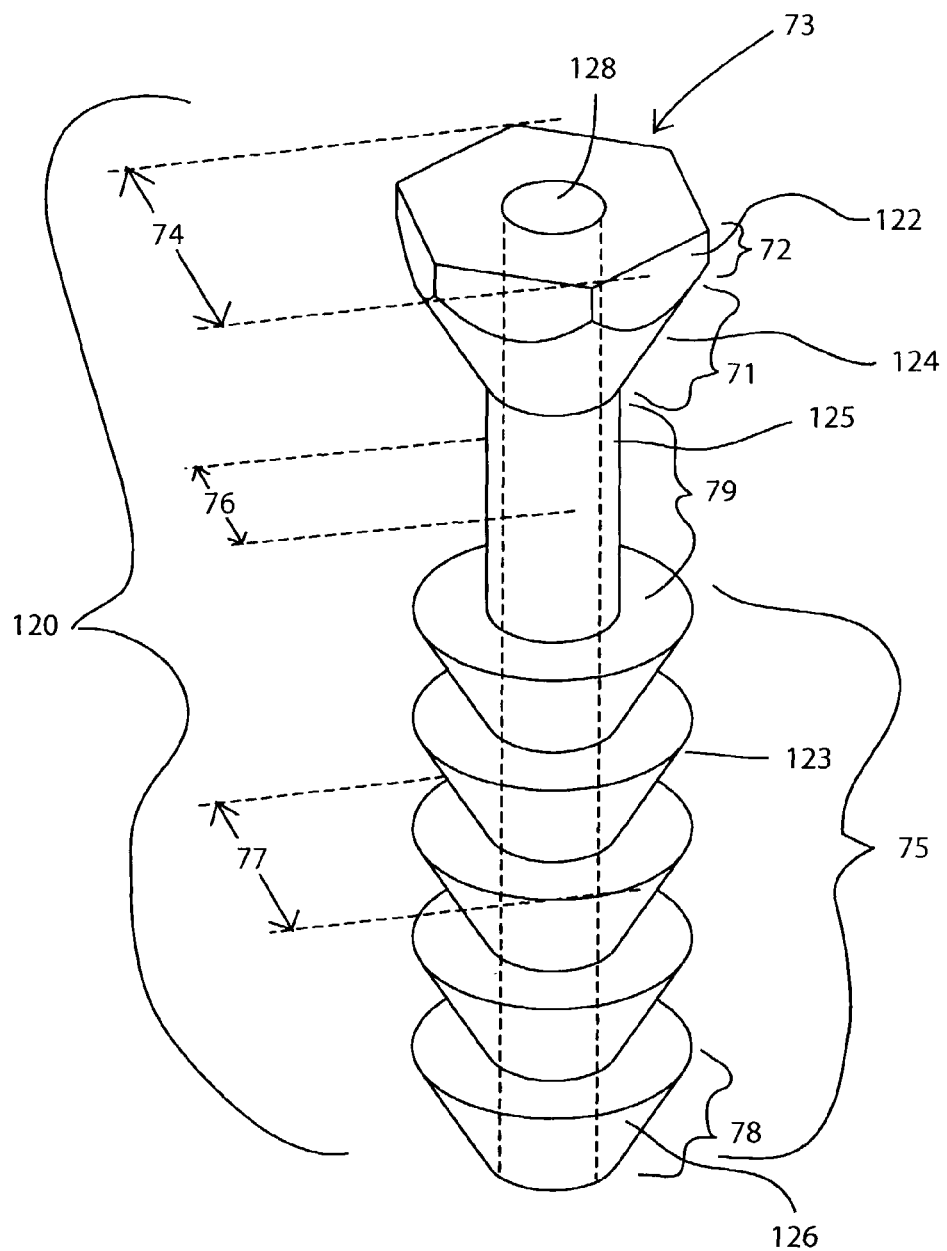
FIG. 14 is perspective view of a barbed fastener.

Different fastening device designs that are well known in the art can be functional as fasteners 70 and 80. The basic common elements of the fasteners 70 and 80 are seen in the example of a threaded fastener 100 in shown in FIG. 13 and a barbed fastener 120 shown in FIG. 14.

The threaded fastener 100, and the barbed fastener 120 both have a head 73 comprising a head diameter 74, a drive feature 72 and a head underside 71. The drive feature in the threaded fastener 100 is an internal female hex drive feature 102. The drive feature in the barbed fastener 120 is an external male drive feature 122. The shape of the underside 71 of the barbed fastener 120 is a chamfer cut 124 and the underside of the threaded fastener 100 is rounded cut 104. The underside 71 shape of both the threaded fastener 100 and the barbed fastener 120 examples are dimensioned to mate with shapes of the first opening 31 and the second opening 32 in the link 30.

Directly adjacent to the head 72 on both threaded fastener 100 and the barbed fastener 120 is a fastener shaft 79 with a shaft diameter 76. Protruding from the shaft 79 is the aforementioned engager 75 with a fixation outer diameter 77. This fixation diameter varies depending on the bone that is being treated and the size of the patient. Typically this diameter is from 1 mm to 10 mm. The shaft diameter 76 can be an undercut shaft 125, as shown in the barbed fastener 120, with a diameter 75 smaller than the fixation outer diameter 77. The shaft diameter can also be a run out shaft 105 as shown in the threaded fastener 100 with a diameter 76 larger than or equal to the fixation diameter 77. In either case, the shaft diameter 76 is smaller than the head diameter 74. This allows fasteners 70 and 80 to be captured and not pass completely through the openings 31 and 32 in the link 30.

In the case of the threaded fastener 100, the engager 75 comprises at least one helical thread form 103. Although the example of a unitary continuous helical thread 103 is shown, it is understood that multiple lead helical threads, discontinuous helical threads, variable pitch helical threads, variable outside diameter helical threads, thread-forming self-tapping, thread-cutting self-tapping, and variable root diameter helical threads can be interchanged and combined to form an optimized engager 75 on the threaded fastener 100. The engager 75 on the barbed fastener 120 is shown as a uniform pattern of connected truncated conical sections 123. However, it is understood that different barbed fastener designs known in the art such as superelastic wire arcs, deformable barbs, radially expandable barbs, and barbs with non-circular cross-sections can be interchanged and combined to form a optimized engager 75 on the barbed fastener 120.

Protruding from the engager 75 at the distal end of both the threaded fastener 100 and the barbed fastener 120 is a fastener tip 78. The fastener tip 78 can either be a smooth conical tip 126 as shown in the barbed fastener 120, or a cutting tip 106 as shown on the threaded fastener 100. Although a cutting flute tip is shown as the cutting tip 106 on the threaded fastener, other cutting tips designs including gimble and spade tips can be used.

In the example of the barbed fastener 120, a canulation bore 128 passes though the head 71, the shaft 79, the engager 75, and the tip 78. This canulation bore 128 allows placement of the fasteners 70 and 80 over the guide pins 40 and 50. Although not shown on the example of the threaded fastener 100 in FIG. 13, it is understood that the fasteners 70 and 80, regardless of their other features, can either be of the cannulated design shown in the barbed fastener 120 example or a non-cannulated design as shown in the threaded fastener 100 example.

Fasteners 70 and 80 can be made in a variety of different ways using a variety of one or more different materials. By way of example and not by limitation, Fasteners 70 and 80 can be made from medical grade biodegradable or non-biodegradable materials. Examples of biodegradable materials include biodegradable ceramics, biological materials, such as bone or collagen, and homopolymers and copolymers of lactide, glycolide, trimethylene carbonate, caprolactone, and p-dioxanone and blends or other combinations thereof and equivalents thereof. Examples of non-biodegradable materials include metals such as stainless steel, titanium, Nitinol, cobalt, alloys thereof, and equivalents thereof and polymeric materials such as non-biodegradable polyesters, polyamides, polyolefins, polyurethanes, and polyacetals and equivalents thereof.

All the design elements of the threaded fastener 100 and barbed fastener 120 are interchangeable. Hence either of the fasteners 70 and 80 can comprise of any combination of the design elements described for the threaded fastener 100 and the barbed fastener 120. By way of one example, the first fastener 70 can be made from a bioabsorbable copolymer of lactide and glycolide and structurally comprise an external male drive feature 122, a run out shaft 105, a multiple-lead, non-continuous helically threaded engager 75, with a cutting flute tip 106 and a continuous emulation 128. Likewise the second fastener 80 can be made from a different combination of the features used to describe the threaded fastener 100 and the barbed fastener 120.

Although the examples of barbed connected truncated conical sections 123 and helical thread forms 103 are shown by example to represent the bone engager 75, it is understood that other means of engaging bone can be used for the engager 75. These means include nails, radially expanding anchors, pressfits, tapers, hooks, surfaces textured for biological ingrowth, adhesives, glues, cements, hydroxyapitite coated engagers, calcium phosphate coated engagers, and engagers with tissue engineered biological interfaces. Such means are known in the art and can be used as alternative bone engagement means for the first bone engager 75 on the first fastener 70 or the second bone engager 85 on the second fastener 80.

Different embodiments of the bone alignment implant 15 invention allow for different means of relative movement between the two bone sections 2 and 3. Nine embodiments of the bone alignment implant 15 are shown in FIG. 15 through FIG. 23. These embodiments are labeled 15A through 15I.

Figure 15:
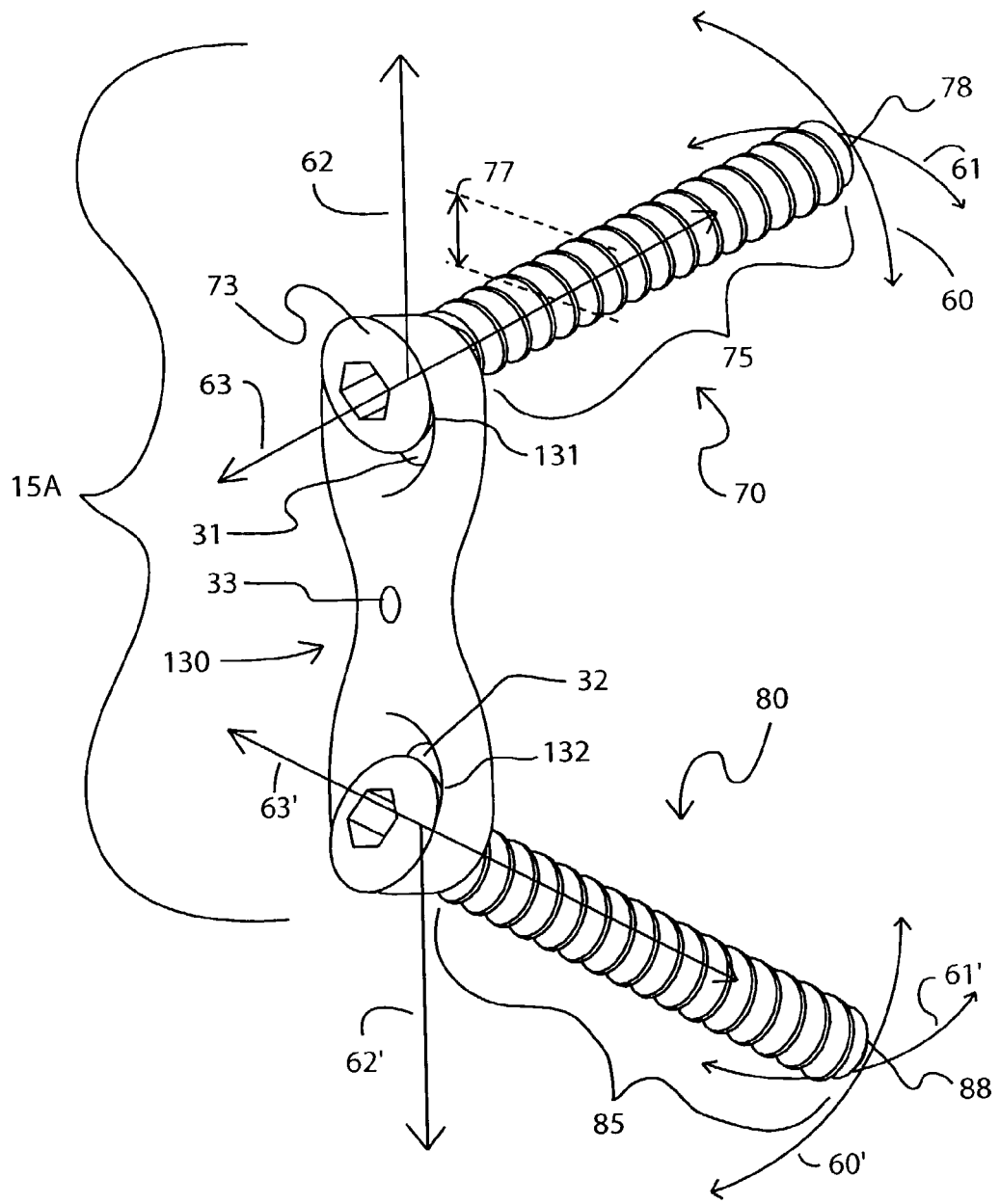
FIG. 15 is perspective view of an alternative embodiment of the bone alignment implant with rigid link and fasteners, with joints allowing restricted movement between them.

In a rigid-bodies embodiment 15A shown in FIG. 15, both the link 30 and the fasteners 70 and 80 are rigid, but a first connection 131 and a second connection 132 between each of them allows for relative movement between the link 30 and the fasteners 70 and 80 resulting in relative movement between the bone sections 2 and 3. In embodiments 15B, 15C, and 15D of this invention shown in FIG. 16, FIG. 17 and FIG. 18, the link 30 is deformable allowing the fasteners 70 and 80 to move with the bone sections 2 and 3. In embodiments 15E and 15F shown in FIG. 19 and FIG. 20, the connections between the link 30 and the fasteners 70 and 80 along with the deformable link 30 allow the fasteners 70 and 80 to move with the bone sections 2 and 3. In an embodiment 15G shown in FIG. 21, the fasteners 70 and 80 are deformable allowing movement of the bone sections 2 and 3. In embodiments 15H and 15I shown in FIG. 22 and FIG. 23, the fasteners 70 and 80 are fixed to a flexible link 30.

A rigid-bodies embodiment 15A of the bone alignment implant 15 is shown in FIG. 15. In the rigid-bodies embodiment 15A, the link 30 is a rigid link 130. In the rigid bodies embodiment 15A, the first fastener 70 is free to rotate about its axis or tilt in a first tilt direction 60 or a second tilt direction 61 and is partially constrained to move in a longitudinal direction 62 by the confines of the size of the first opening 31 and the first shaft diameter 77, and partially constrained to move in the axial direction by the confines of the size of the first opening and the diameter 74 of the head 73 of the first fastener 70. The first opening 31 is larger in the longitudinal direction 62 than is the shaft diameter 77 of the first fastener 70. This allows for relative movement at the first joint 131 in a combination of tilt in the first direction 60, tilt in the second direction 61, and translation in the axial direction 63.

Similar tilt and translation is achieved between the second fastener 80 and the link 30 at the second joint 132. The second fastener 80 is also free to rotate or tilt in a first tilt direction 60' or a second tilt direction 61' and is partially constrained to move in a longitudinal direction 62' by the confines of the size of the second opening 32 and the shaft diameter of the second fastener 80. The second opening 31 is larger in the longitudinal direction 62' than is the shaft diameter of the second fastener 70. This allows for relative movement at the second joint 132 in a combination of tilt in the first direction 60' and tilt in the second direction 61' and limited translation in the axial direction 63'.

The combination of relative movement between the first joint and the second joint allows for relative movement between the bone sections 2 and 3 when the rigid bodies embodiment 15A of the bone alignment implant 15 is clinically applied across an active physis 1.

Figure 16:
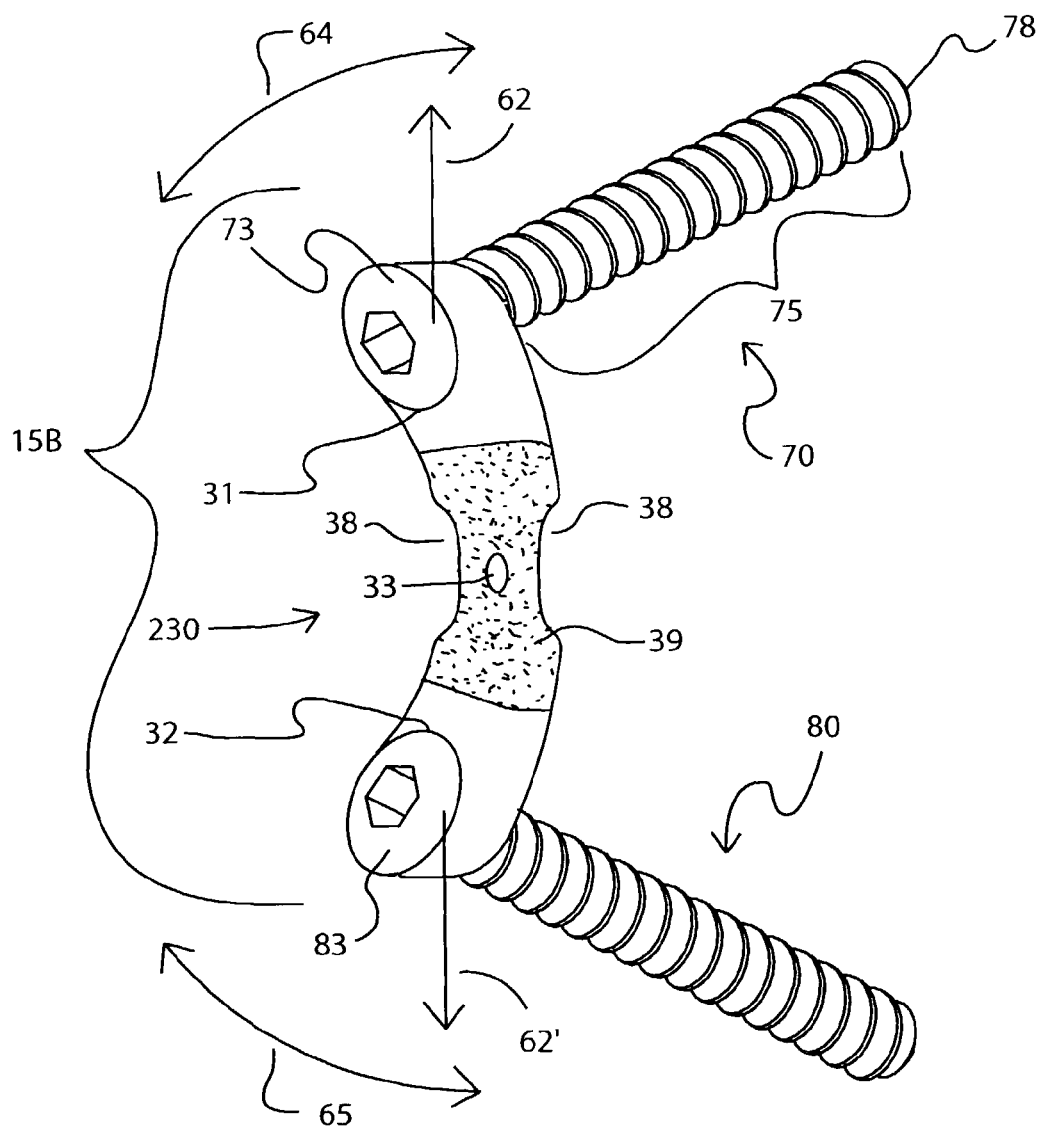
FIG. 16 is a perspective view of an alternative embodiment of the bone alignment implant showing a flexible midsection of the link with rigid material surrounding the openings.

A flexible link embodiment 15B of the bone alignment implant 15 is shown in FIG. 16. In the deformable link embodiment 15B, the link 30 is represented by a deformable link 230 that allows deformation of the section 2 and 4 as the physis 1 grows in a first bending direction 64 and a second bending direction 65. However, the maximum length between the first opening 31 and the second opening 32 of the deformable link 230 limits the longitudinal displacement 62 between the head 73 of the first fastener 70 and the longitudinal displacement 62' between the head 83 of the second fastener 80. Since the heads 73 and 83 are coupled to the respective bone engagers 75 and 85, and the bone engagers 75 and 85 are implanted into the respective bone segments 2 and 3, the maximum longitudinal displacement of the bone segments 2 and 3 is limited by the deformed length between the first opening 31 and second opening 32 of the link 30, and the flexibility and length of the fasteners 70 and 80.

Also shown in FIG. 16 is a material differential area 38 on the link 30. The material differential area 38 is an area on the link 30 where material is either added to the link 30 or removed from the link 30 in relationship to the desired mechanical properties of a central section 39 of the link 30. The central section 39 is made stiffer by adding material to the material differential area 38.

The central section 39 is made more flexible by removing material from the material differential area 38. Similarly the central section 39 is made stiffer by holding all other variables constant and decreasing the size of the guide opening 33. The central section 39 is made more flexible by increasing the size of the guide opening 33. Hence the desired stiffness or flexibility of the link 30 is regulated by the relative size of the material removed or added at the material differential areas 37 and 38 and the relative size of the guide opening 33 with respect to the outer periphery 34 in the central section 39 of the link 30.

It is also understood that the relative stiffness and strength of the link 30 and structural elements such as the central section 39 is dependent on the material from which it is made. The link 30 and structural elements such as the central section 39 therein can be made in a variety of different ways using one or more of a variety of different materials. By way of example and not by limitation, the central section 39 can be made from medical grade biodegradable or non-biodegradable materials. Examples of biodegradable materials include biodegradable ceramics, biological materials, such as bone or collagen, and homopolymers and copolymers of lactide, glycolide, trimethylene carbonate, caprolactone, and p-dioxanone and blends or other combinations thereof and equivalents thereof. Examples of non-biodegradable materials include metals such as titanium alloys, zirconium alloys, cobalt chromium alloys, stainless steel alloys, Nitinol alloys, or combinations thereof, and equivalents thereof and polymeric materials such as non-biodegradable polyesters, polyamides, polyolefins, polyurethanes, and polyacetals and equivalents thereof.

Figure 17:
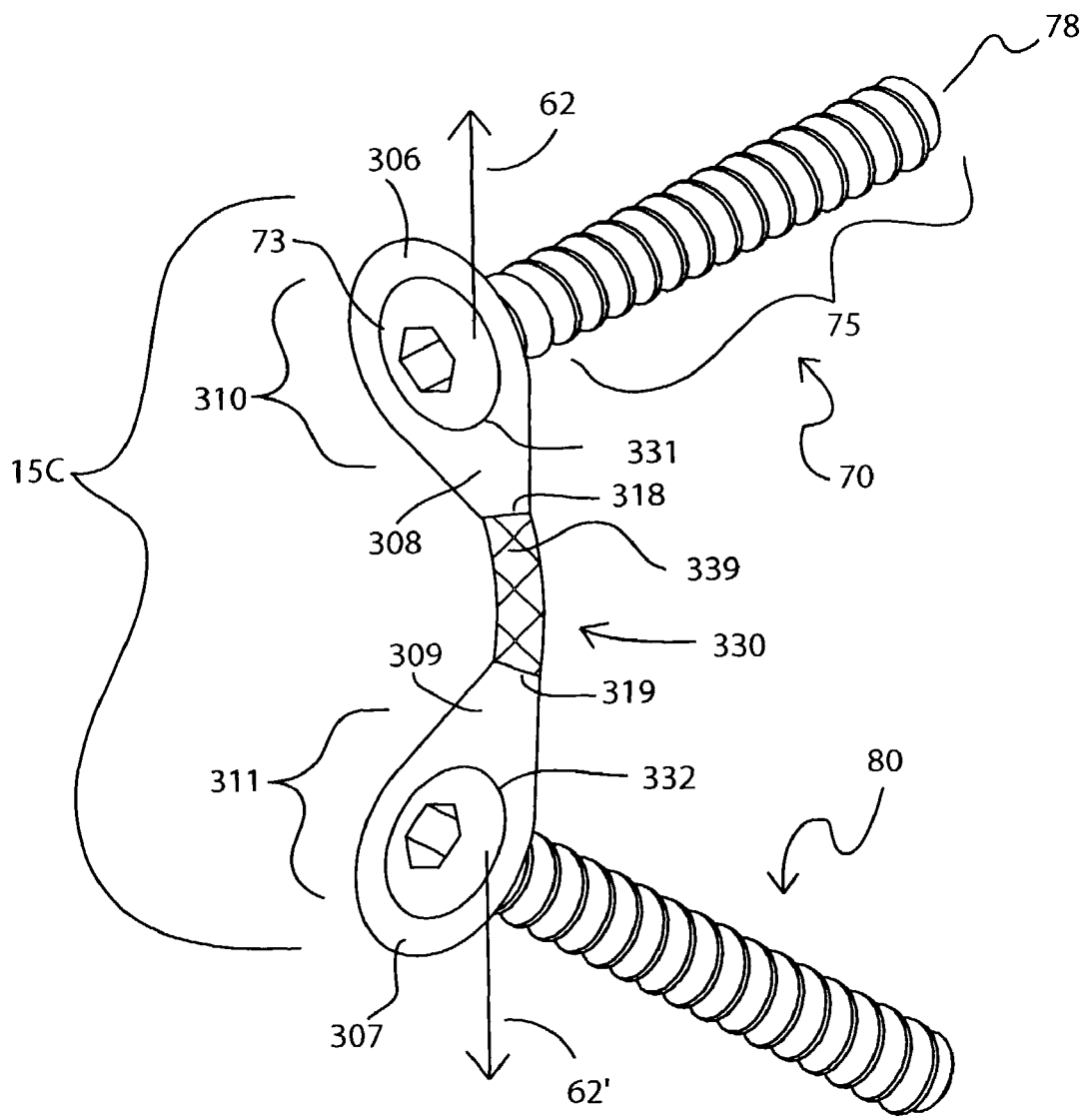
FIG. 17 is a perspective view of an alternative embodiment of the bone alignment implant showing a flexible midsection of the link made from a separate flexible member with rigid material surrounding the openings.

FIG. 17 shows a flexible cable embodiment 15C of the bone alignment implant 15. The flexible cable embodiment 15C comprises a flexible cable link 330 joined to the first fastener 70 by a first eyelet 306 on the first side 310 and joined to the second link 80 by a second eyelet 307 on the second side 311. The first eyelet 306 has a first opening 331 through which the first fastener 70 passes. The second eyelet 307 has a second opening 332 through which the second fastener 80 passes. A flexible member 339 connects the first eyelet 306 to the second eyelet 307. The flexible member 339 allows relative movement between the first eyelet 306 and the second eyelet 307, except the longitudinal displacement 62 and 62' is limited by the length between the first opening 331 and the second opening 332. This is proportional to the length of the flexible member 339.

The flexible member 339 is connected to the first eyelet 306 and the second eyelet 307 by means of joined connections 318 and 319. These joined connections 318 and 319 are shown as crimped connections in this example. However, the flexible member 339 can be joined to the link 30 by other means such as insert molding, welding, soldering, penning, pressfitting, cementing, threading, or gluing them together.

Figure 18:
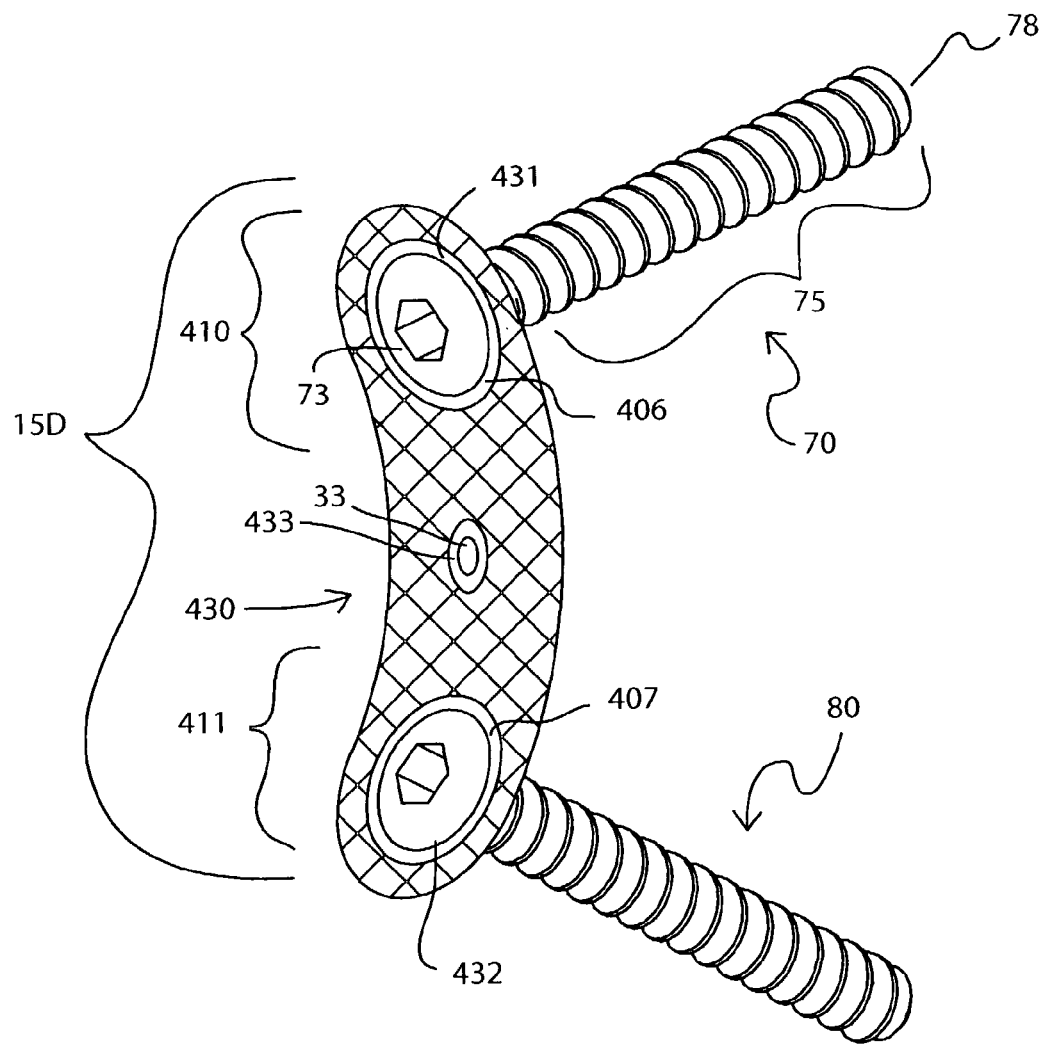
FIG. 18 is a perspective view of an alternative embodiment of the bone alignment implant showing flexible woven material throughout the body of the link with reinforcement grommets surrounding the openings.

FIG. 18 shows a flexible fabric embodiment 15D of the bone alignment implant 15. The flexible fabric embodiment 15D comprises a flexible fabric link 430 joined to the first fastener and the second fastener 80. The flexible fabric link 430 comprises a first grommet 406 on a first side 410 and joined to the second link 80 by a second grommet 407 on a second side 411. The first grommet 406 has a first opening 431 through which the first fastener 70 passes. The second grommet 407 has a second opening 432 through which the second fastener 80 passes. A flexible fabric 439 connects the first grommet 406 to the second grommet 407. The flexible fabric 439 allows relative movement between the first grommet 406 and the second grommet 407, except the longitudinal displacement 62 is limited by the length between the first opening 431 and the second opening 432. A guide hole grommet 433 may be employed to reinforce the guide pin opening 33.

The grommets function as reinforcement structures that prevent the flexible fabric from being damaged by the fasteners 70 and 80. The grommets can be made from medical grade biodegradable or non-biodegradable materials. Examples of materials from which the grommet can be made are similar to those bioabsorbable and non-biodegradable materials listed as possible materials for the fasteners 70 and 80.

The flexible fabric 439 comprises woven or matted fibers of spun medical grade biodegradable or non-biodegradable materials. A wide variety of materials may be used to make the flexible fabric 439. For example, wire, fibers, filaments and yarns made therefrom may be woven, knitted or matted into fabrics. In addition, even non-woven structures, such as felts or similar materials, may be employed. Thus, for instance, nonabsorbable fabric made from synthetic biocompatible nonabsorbable polymer yarns, made from polytetrafluorethylenes, polyesters, nylons, polyamides, polyolefins, polyurethanes, polyacetals and acrylic yarns, may be conveniently employed. Similarly absorbable fabric made from absorbable polymers such as homopolymers and copolymers of lactide, glycolide, trimethylene carbonate, caprolactone, and p-dioxanone and blends or other combinations thereof and equivalents thereof may be employed. Examples of non-biodegradable non-polymeric materials from which the flexible fabric can be made include metals such as stainless steel, titanium, Nitinol, cobalt, alloys thereof, and equivalents thereof.

Figure 19:
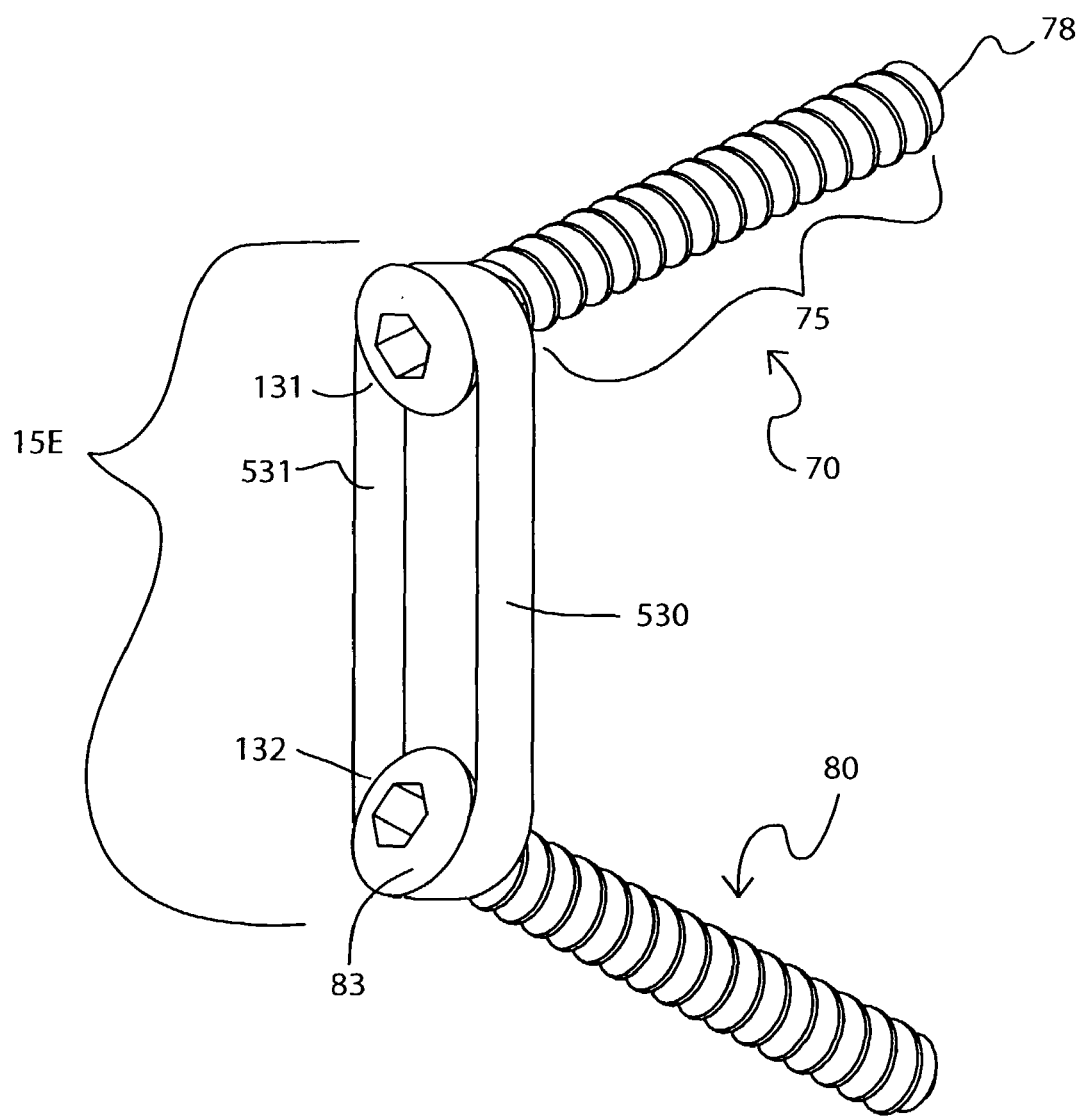
FIG. 19 is a perspective view of an alternative embodiment of the bone alignment implant showing the link made from a flexible band of material.

A band embodiment 15E is shown in FIG. 19 in which a band 530 that is a continuous loop or band of material that functions as the link 30. The band embodiment 15E allows both movement at the first joint 131 and second joint 132 and allows deformation within the link 30. The shafts 79 of the first fastener 70 and second fastener 80 are both positioned in the inside 531 of the band 530. The band can be either a fabric band made from the same materials described for the flexible fabric 439 of the flexible fabric embodiment 15D, or the band 530 can be a unitary, continuous loop of a given biocompatible material such as a bioabsorbable polymer, non-biodegradable polymer, metal, ceramic, composite, glass, or biologic material.

In the band embodiment 15E, the band 530 tethers between the head 73 of the first fastener 70 and the head 83 of the second fastener as the physeal tissue 90 generates and the bone in aligned. One advantage of the band embodiment 15E is that after the desired alignment is obtained, the band 530 can be cut and removed without removing the fasteners 70 and 80. Furthermore, as with all of the embodiments of the bone alignment device 15A, 15B, 15C, 15D, 15F, 15G, 15H and 15I, the fasteners 70 and 80 can be made from a biodegradable material and left in place to degrade.

Figure 20:
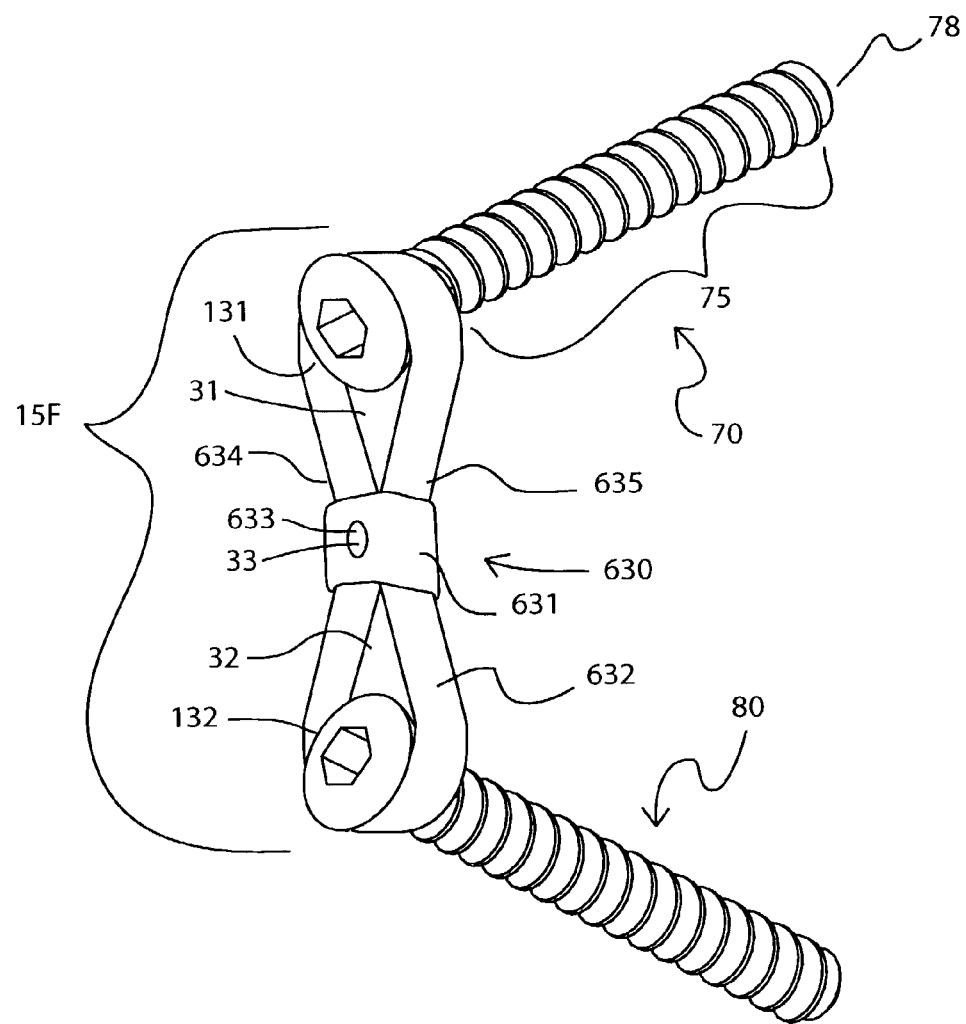
FIG. 20 is a perspective view of an alternative embodiment of the bone alignment implant showing the link made from a flexible ring of braided material that is joined in the midsection, forming two openings.

A crimped band embodiment 15F of the bone alignment device 15 is shown in FIG. 20. The crimped band embodiment 15F is similar to the band embodiment 15E in that it allows both movement at the first joint 131 and second joint 132. The crimped band embodiment 15F comprises a crimped band link 630 that comprises a band 632 that loops around the head 73 of the first fastener 70 and the head 83 of the second fastener 80. However, the link 30 in the crimped band embodiment 15F has an additional ferrule feature 631 comprising a loop of deformable material that brings a first side 634 and a second side 635 of the band together forming the first opening 32 and the second opening 32. A bore 633 in the midsection of the ferrule 631 passes through the crimped band link 630 to form the aforementioned guide pin hole 33.

As with the band embodiment 15E, an advantage of the band embodiment 15E is that after the desired alignment is obtained, the band 632 can be severed across the boundaries of the first opening 31 and the boundaries of the second opening 32. This provides a means for the crimped band link 630 to be removed without removing the fasteners 70 and 80.

Figure 21:
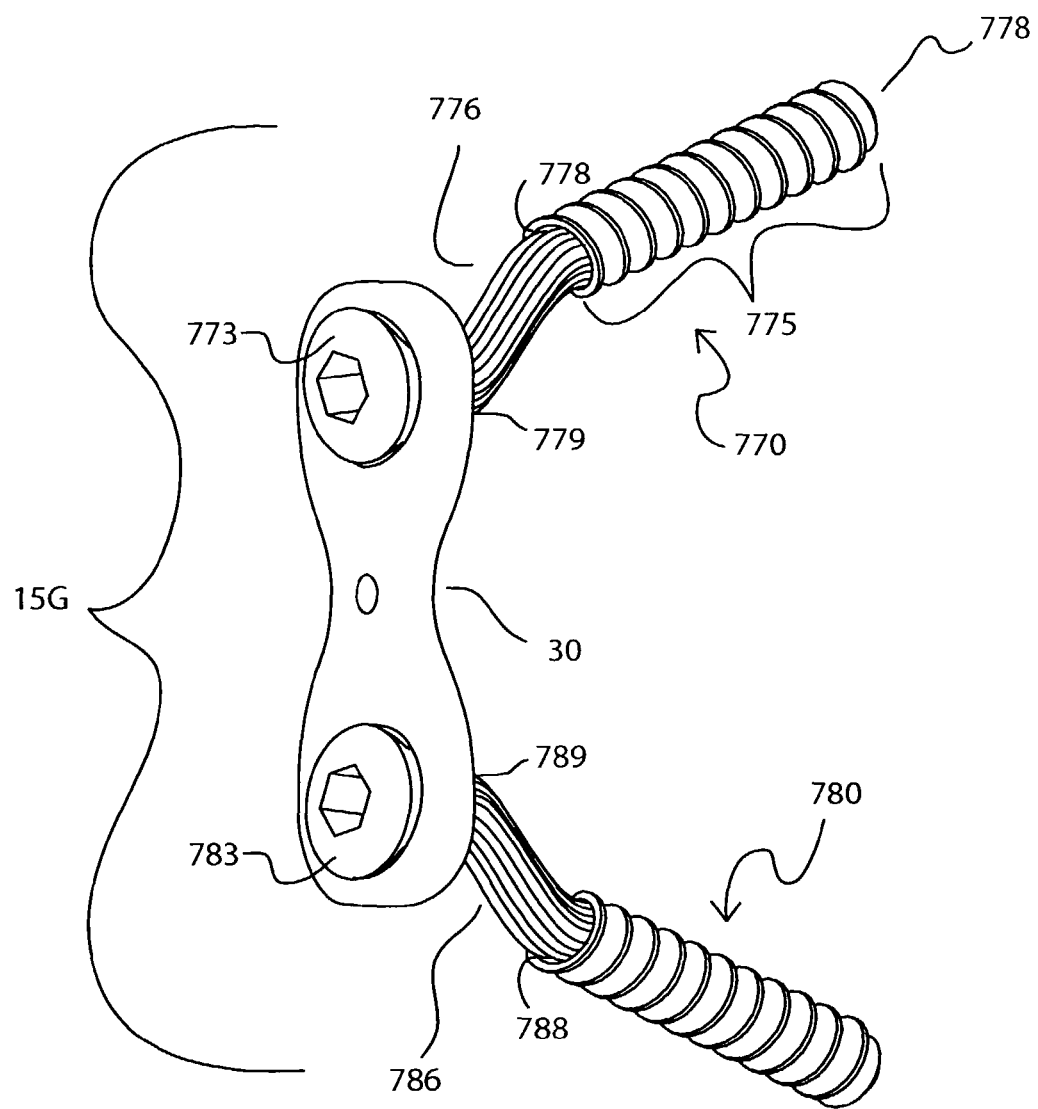
FIG. 21 is a side view of an alternative embodiment of the bone alignment implant showing a bone fasteners that have flexible shaft sections.

A deformable fastener embodiment 15G is shown in FIG. 21. The deformable fastener shaft embodiment 15G comprises a first deformable fastener 770 with a deformable shaft 776, a link 30 and a second fastener 80. The second fastener 80 may also have a deformable shaft 786 as shown in the deformable fastener embodiment 15G. However, it may also have a nondeformable shaft. The second fastener 80 may also be in the design or material of any of the combinations of aforementioned threaded fasters 100 or barbed fasteners 120. Likewise, the second fastener 80 can have a flexible shaft 786, as shown in the example of the deformable fastener embodiment 15G in FIG. 21, and the first fastener 70 can be in the design or material of any of the combinations of aforementioned threaded fasters 100 or barbed fasteners 120.

The flexibility of the flexible shaft 776 and 786 of the fasteners 70 and 80 can be simply a result of the material selection of the flexible shaft 776 and 786, or can be the result of a design that allows for flexibility of the shaft. For example, the flexible shaft 776 and 786 can be manufactured from a material such as the aforementioned biocompatible polymeric materials or superelastic metallic materials such as Nitinol that would deform under the loads associated with bone alignment. The flexible shafts 776 and 786 could also be manufactured from biocompatible materials typically not considered to be highly elastic such as stainless steel, titanium, zirconium, cobalt chrome and associated alloys thereof, and shaped in the form of a flexible member such as cable, suture, mesh, fabric, braided multifilament strand, circumferentially grooved flexible shaft, filament, and yarn.

Connections 778 and 788 between the flexible shafts 776 and 786 and the associated engagers 775 and 780 of the fasteners 70 and 80 can be unitary and continuous, as is typically the case for fasteners 70 and 80 made entirely from the aforementioned biocompatible polymeric materials and superelastic metallic materials. The connections 778 and 788 can also be joined connections as is the case for flexible shafts 776 and 786 made from flexible members. Although the example of a pressfit connection is shown as the means of the connections 778 and 788 in the deformable fastener embodiment 15G shown in FIG. 21, these joined connections 778 and 788 can be crimped, welded, insert molded, soldered, penned, pressfit, cemented, threaded, or glued together.

Heads 773 and 783 are connected to the respective flexible shafts 776 and 786 by respective head connections 779 and 789. These head connections 779 and 789 can also be unitary and continuous, as again is typically the case of fasteners 70 and 80 made entirely from the aforementioned biocompatible polymeric materials and superelastic metallic materials. The head connections 779 and 789 can also be joined connections, as is the case for flexible shafts 776 and 786 made from flexible members. Although the example of a pressfit connection is the means of the connections 779 and 789 in the deformable fastener embodiment 15G shown in FIG. 21, these joined connections 779 and 789 can also be crimped, insert molded, welded, soldered, penned, pressfit, cemented, threaded, or glued together.

Figure 22:
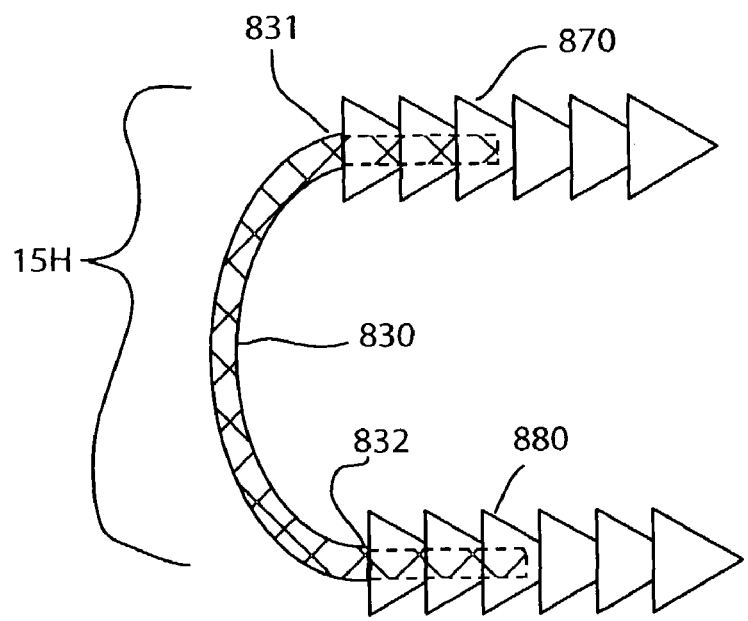
FIG. 22 is a side view of an alternative embodiment of the bone alignment implant showing two barbed bone fasteners attached to a flexible link.
Figure 23:
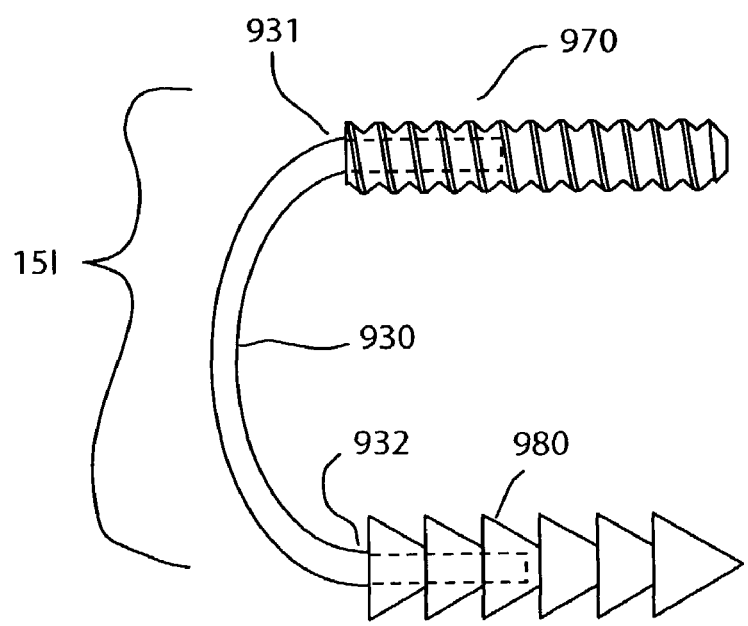
FIG. 23 is a side view of an alternative embodiment of the bone alignment implant showing one barbed bone fastener and one threaded bone fastener connected to a flexible link.

Embodiments of the bone alignment implant 15 are shown in FIGS. 22 and 23 in which the first fastener 70 and second fastener 80 are fixedly joined to the link 30 that is flexible.

A paired fastener embodiment 15H is shown in FIG. 22 in which similar designs of paired fasteners 870 and 880 are fixedly joined to a flexible link 830 by means of joined connections 831 and 832. These joined connections 831 and 832 are shown as insert molded connections in this example in which the link is formed within the fastener by means of molding the molded fasteners 870 and 880 around the flexible link 830. However, the pair fasteners 870 and 880 can be joined to the link 830 by other means such as crimping, welding, soldering, penning, pressfitting, cementing, threading, or gluing.

In the paired fastener embodiment 15H, the first paired fastener 870 and the second paired fastener 880 are shown in FIG. 22 as barbed style fasteners similar to the aforementioned barbed fastener 120. However, the paired fasteners 870 and 880 can also be similar to the aforementioned threaded fastener 100 or can comprise of any combination of the design elements described for the threaded fastener 100 and the barbed fastener 120.

A non-paired fastener embodiment 15I is shown in FIG. 23 in which different designs of fasteners 970 and 980 are fixedly joined to a flexible link 930 by means of joined connections 931 and 932. These joined connections 931 and 932 are shown as insert molded connections in this example in which the link is formed within the fastener by means of molding the molded fasteners 970 and 980 around the flexible link 930. However, the fasteners 970 and 980 can be joined to the link by other means such as crimping, welding, soldering, penning, pressfitting, cementing, threading, or gluing.

While the present invention has been disclosed in its preferred form, the specific embodiments thereof as disclosed and illustrated herein are not to be considered in a limiting sense as numerous variations are possible. The invention may be embodied in other specific forms without departing from its spirit or essential characteristics. The described embodiments are to be considered in all respects only as illustrative and not restrictive. No single feature, function, element or property of the disclosed embodiments is essential. The scope of the invention is, therefore, indicated by the appended claims rather than by the foregoing description. The following claims define certain combinations and subcombinations that are regarded as novel and non-obvious. Other combinations and subcombinations of features, functions, elements and/or properties may be claimed through amendment of the present claims or presentation of new claims in this or a related application. Such claims, whether they are broader, narrower or equal in scope to the original claims, are also regarded as included within the subject matter of applicant's invention. All changes that come within the meaning and range of equivalency of the claims are to be embraced within their scope.

What is claimed is:

1. A bone alignment implant system comprising:
   an elongated link having a top surface and an opposing bottom surface that each extend between a first side edge and an opposing second side edge and which extend between a first end and an opposing second end of the link, the link having a first opening extending completely therethrough between the top surface and the bottom surface at the first end, a second opening extending completely therethrough between the top surface and the bottom surface at the second end and a guide opening extending completely therethrough between the top surface and the bottom surface at a central location between the first opening and the second opening, the first opening, the second opening, and the guide opening being completely encircled by the link, the guide opening being smaller than the first opening and the second opening, the link having a central linear longitudinal axis extending between the first end and the opposing second end that intersects with the first opening, the second opening, and the guide opening, the first opening also having a central linear axis extending therethrough that extends normal to the bottom surface of the link, a first recess being centrally formed on the first side edge and a second recess being centrally formed on the second side edge such that a linear line extending orthogonal to the central linear longitudinal axis can extend between the first recess and the second recess and intersect with the guide opening, the first recess and the second recess each extending from the top surface to the bottom surface of the link;
   a first bone fastener comprising a first head at one end and a first engager projecting from an opposing end, the first engager being passable though the first opening, and the first head being precluded from passing through the first opening; and
   a second bone fastener comprising a second engager and a second head, the second engager being passable through the second opening, and the second head being precluded from passing through the second opening, wherein neither the first engager nor the second engager can pass though the guide opening, wherein the first opening, the second opening, and the guide opening are the only openings formed on the link that extend completely through the link and are completely encircled by the link.

2. The bone alignment implant system as recited in claim 1, wherein the link, the first bone fastener, and the second bone fastener are each comprised of a medical grade material.

3. The bone alignment implant system as recited in claim 1, wherein the first engager and the second engager each have a transverse cross sectional area that is configured so that neither the first engager nor the second engager can pass through the guide opening.

4. The bone alignment implant system as recited in claim 1, wherein the first head of the first bone fastener can freely rotate and pivot when the first head is seated within the first opening of the link.

5. The bone alignment implant system as recited in claim 1, wherein the first engager and the second engager each comprise a helical thread.

6. The bone alignment implant system as recited in claim 1, wherein the first bone fastener and the second bone fastener each comprise a screw.

7. The bone alignment implant system as recited in claim 1, wherein the link has a bottom surface with a plurality of spikes projecting therefrom.

8. The bone alignment implant system as recited in claim 1, further comprising a guide wire having a distal end adapted to slidably pass through the guide opening.

9. The bone alignment implant system as recited in claim 1, wherein the second opening also having a central linear axis extending therethrough that extends normal to the bottom surface of the link.

10. The bone alignment implant system as recited in claim 1, wherein the bottom surface of the link is smooth with no projections outwardly extending therefrom.

11. The bone alignment implant system as recited in claim 1, wherein the top surface of the link is complementary to the bottom surface of the link.

12. The bone alignment implant system as recited in claim 1, wherein the first bone fastener and the second bone fastener each comprise a cannulated screw.

13. An orthopedic bone alignment implant system comprising:
a link having a top surface and a bottom surface between which a first opening, a second opening, and a guide opening extend so as to pass completely through the link and so as to be completely encircled by the link, the guide opening being centrally positioned between the first opening and the second opening and being smaller than the first opening and the second opening, the top surface and the bottom surface each extending between a first side edge and an opposing second side edge which in turn extend between a first end and an opposing second end of the link, a first recess being formed on the first side edge and a second recess being formed on the second side edge such that a linear line can extend between the first recess and the second recess so as to intersect with the guide opening, the first recess and the second recess each extending from the top surface to the bottom surface of the link, the bottom surface being smooth with no projections outwardly extending therefrom;
a first fastener and a second fastener each having a head at one end and a bone engager projecting from an opposing end;
wherein the first and second openings in the link are dimensioned to allow the bone engager of the first fastener and the second fastener to pass therethrough and the first opening, the second opening, and the guide opening are the only openings formed on the link that extend completely through the link and are completely encircled by the link.

14. The bone alignment implant system as recited in claim 13, wherein the guide opening is configured so that the bone engager of the first fastener and the second fastener cannot pass therethrough.

15. The bone alignment implant system as recited in claim 13, wherein the first head of the first bone fastener can freely rotate and pivot when the first head is seated within the first opening of the link.

16. The bone alignment implant system as recited in claim 13, wherein the first opening, the second opening, and the guide opening are aligned along a linear longitudinal axis that centrally extends between the first end and the opposing second end of the link, the linear line extending orthogonal to the linear longitudinal axis.

17. The bone alignment implant system as recited in claim 13, wherein the bone engager of the first fastener and the second fastener each comprise a helical thread.

18. The bone alignment implant system as recited in claim 13, further comprising a guide wire having a distal end adapted to slidably pass through the guide opening.

19. The bone alignment implant system as recited in claim 13, further comprising:
the bone engager of the first fastener is adapted to connect to a epiphyseal section of bone on a first side of a physis;
the bone engager of the second fastener is adapted to connect to a metaphyseal section of bone on a second side of the physis; and
the link being adapted to span the between the epiphyseal section of bone on the first side of the physis and the metaphyseal section of bone on the second side of the physis.

20. The bone alignment implant system as recited in claim 13, wherein the first opening and the second opening each have a central linear axis extending therethrough that extends normal to the bottom surface of the link.

21. The bone alignment implant system as recited in claim 13, wherein the link has a substantially FIG. 8 configuration.

22. The bone alignment implant system as recited in claim 13, wherein the top surface of the link is complementary to the bottom surface of the link.

23. The bone alignment implant system as recited in claim 13, wherein the first bone fastener and the second bone fastener each comprise a cannulated screw.

24. An orthopedic bone alignment implant system comprising:
a link having a top surface and a bottom surface between which a first opening, a second opening, and a guide opening extend so as to pass completely through the link and so as to be completely encircled by the link, the guide opening being centrally positioned between the first opening and the second opening and being smaller than the first opening and the second opening, the top surface and the bottom surface each extending between a first side edge and an opposing second side edge which in turn extend between a first end and an opposing second end of the link, the first opening, the second opening, and the guide opening being aligned along a linear longitudinal axis that centrally extends between the first end and the opposing second end of the link, a first recess being formed on the first side edge and a second recess being formed on the second side edge such that a linear line extending orthogonal to the linear longitudinal axis can extend between the first recess and the second recess so as to intersect with the guide opening, the first recess and the second recess each extending from the top surface to the bottom surface of the link, the bottom surface being smooth with no projections outwardly extending therefrom;
a first fastener and a second fastener each having a head at one end and a bone engager projecting from an opposing end;
wherein the first and second openings in the link are dimensioned to allow the bone engager of the first fastener and the second fastener to pass therethrough and wherein the first opening, the second opening, and the guide opening are the only openings formed on the link that extend completely through the link and are completely encircled by the link;
wherein the guide opening is configured so that the bone engager of the first fastener and the second fastener cannot pass therethrough.

* * * * *

UNITED STATES PATENT AND TRADEMARK OFFICE
CERTIFICATE OF CORRECTION

PATENT NO. : 7,811,312 B2  Page 1 of 3
APPLICATION NO. : 10/310720
DATED : October 12, 2010
INVENTOR(S) : Stevens et al.

It is certified that error appears in the above-identified patent and that said Letters Patent is hereby corrected as shown below:

Face
Item 57, ABSTRACT, Line 6, change "as a flexible tethers" to --as flexible tethers--

Drawings
Sheet 16, replace Figure 16 with the figure depicted below, wherein one instance of "38" has been changed to --37--

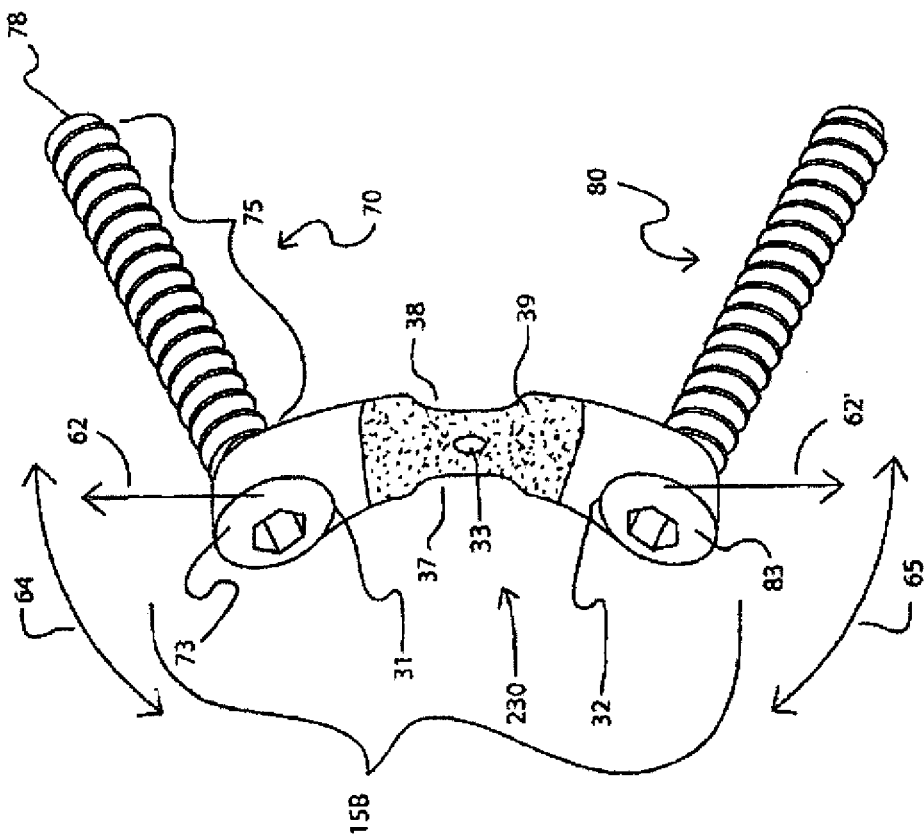

Signed and Sealed this
Eighth Day of May, 2012

David J. Kappos
*Director of the United States Patent and Trademark Office*

CERTIFICATE OF CORRECTION (continued)
U.S. Pat. No. 7,811,312 B2

Column 1
Line 37, change "bore" to --bone--

Column 3
Line 20, change "is anterior" to --is an anterior--
Line 37, change "is a anterior" to --is an anterior--
Line 44, change "is sagittal" to --is a sagittal--
Line 49, change "is perspective" to --is a perspective--
Line 50, change "is perspective" to --is a perspective--

Column 4
Line 6, change "showing a bone fasteners" to --showing bone fasteners--

Column 5
Line 40, change "though" to --through--
Line 63, change "set of spikes" to --set of spikes 36--

Column 6
Line 29, remove the second instance of [than the]

Column 7
Line 5, change "section 3" to --section 2--
Line 14, change "net gain 95" to --net gain 95--
Line 45, change "is rounded" to --is a rounded--
Line 58, change "diameter 75" to --diameter 76--

Column 8
Line 12, change "a" to --an--
Line 20, change "tips" to --tip--
Line 23, change "head 71" to --head 73--
Line 34, change "Fasteners" to --fasteners--
Line 66, change "hydroxyapitite" to --hydroxyapatite--

Column 9
Line 50, change "fastener 70" to --fastener 80--
Line 62, change "section 2 and 4" to --sections 2 and 4--

Column 10
Line 50, change "second link 80" to --second fastener 80--

Column 11
Line 4, change "fastener and the" to --fastener 70 and the--
Line 6, change "second link 80" to --second fastener 80--
Line 60, change "second fastener" to --second fastener 80--
Line 61, change "bone in aligned" to --bone is aligned--

CERTIFICATE OF CORRECTION (continued)
U.S. Pat. No. 7,811,312 B2

Column 12
Line 12, change "first opening 32" to --first opening 31--
Line 16, before "band embodiment 15E" to --crimped band embodiment 15F--
Line 22, after "fastener" remove [shaft]
Line 24, change "second fastener 80" to --second fastener 780--
Line 25, change "80" to --780--
Line 35, change "shaft" to --shafts--
Line 36, change "fasteners 70 and 80" to --fasteners 770 and 780--
Line 51, change "engagers 775 and 780" to --engagers 775 and 785--
Line 52, change "fasteners 70 and 80" to --fasteners 770 and 780--

Column 13
Line 20, change "pair" to --paired--

Column 15
Line 33, after "therefrom;" insert --and--

Column 16
Line 4, change "a epiphyseal" to --an epiphyseal--
Line 8, change "span the between" to --span between--
Line 17, change "FIG. 8" to --figure 8--